(12) United States Patent
Manley et al.

(10) Patent No.: US 8,217,045 B2
(45) Date of Patent: Jul. 10, 2012

(54) ORGANIC COMPOUNDS

(75) Inventors: Paul W. Manley, Basel (CH); Joseph Schoepfer, Basel (CH)

(73) Assignee: Novartis AG, Basel (CH)

( * ) Notice: Subject to any disclaimer, the term of this patent is extended or adjusted under 35 U.S.C. 154(b) by 222 days.

(21) Appl. No.: 12/596,193

(22) PCT Filed: Apr. 17, 2008

(86) PCT No.: PCT/EP2008/054640
§ 371 (c)(1),
(2), (4) Date: Oct. 16, 2009

(87) PCT Pub. No.: WO2008/125691
PCT Pub. Date: Oct. 23, 2008

(65) Prior Publication Data
US 2010/0113467 A1 May 6, 2010

(30) Foreign Application Priority Data
Apr. 17, 2007 (EP) .................................... 07106308

(51) Int. Cl.
*A61K 31/497* (2006.01)
*C07D 401/00* (2006.01)
(52) U.S. Cl. ................. 514/252.14; 514/341; 546/272.7; 544/360
(58) Field of Classification Search ............. 514/252.14, 514/341; 546/272.7; 544/360
See application file for complete search history.

(56) References Cited

U.S. PATENT DOCUMENTS
7,067,514 B2 *  6/2006  Ono et al. ................. 514/227.8
2006/0241149 A1  10/2006  Adams et al.
2009/0286803 A1 * 11/2009  Manley .................... 514/252.19

FOREIGN PATENT DOCUMENTS
WO  WO 2005/070891 A2  8/2005
WO  WO 2006/059234 A2  6/2006
WO  WO 2007/031265 A2  3/2007
WO  WO 2007/104538 A1  9/2007

OTHER PUBLICATIONS
Potashman et al. CAS: 143:211847, 2005.*
* cited by examiner

*Primary Examiner* — Rei-tsang Shiao
(74) *Attorney, Agent, or Firm* — Scott W. Reid

(57) ABSTRACT

The invention relates to naphthalene carboxylic acid and isoquinoline carboxylic acid amides, and related compounds of formula I

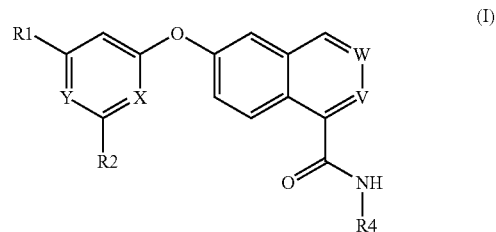

and their uses as pharmaceuticals.

9 Claims, No Drawings

ORGANIC COMPOUNDS

This application is a U.S. National Phase filing of International Application Serial. No. PCT/EP2008/054640 filed 17 Apr. 2008 and claims priority to E.P. Application Serial. No. 07106308.5 filed 17 Apr. 2007, the contents of which are incorporated herein by reference in their entirety.

SUMMARY OF THE INVENTION

The invention relates to naphthalene carboxylic acid and isoquinoline carboxylic acid amides, and related compounds, and their uses as pharmaceuticals. More particularly it relates to compounds, which may be described as naphthalene carboxylic acid and isoquinoline carboxylic acid amides, and related compounds, for use in the treatment of protein kinase dependent diseases, or for their use in the manufacture of pharmaceutical compositions for use in the treatment of said diseases, methods of use of in the treatment of said diseases, pharmaceutical preparations comprising naphthalene carboxylic acid and isoquinoline carboxylic acid amides, and related compounds useful in the treatment of said diseases, naphthalene carboxylic acid and isoquinoline carboxylic acid amides, and related compounds for use in the treatment of said diseases, pharmaceutical preparations comprising these naphthalene carboxylic acid and isoquinoline carboxylic acid amides, and related compounds, processes for the manufacture of the naphthalene carboxylic acid and isoquinoline carboxylic acid amides, and related compounds, the use or methods of use of the naphthalene carboxylic acid and isoquinoline carboxylic acid amides, and related compounds as mentioned above, and/or these naphthalene carboxylic acid and isoquinoline carboxylic acid amides, and related compounds for use in the treatment of the animal or human body. The invention relates to other subject matter as disclosed below.

BACKGROUND OF THE INVENTION

Protein kinases (PKs) are enzymes which catalyze the phosphorylation of specific serine, threonine or tyrosine residues in cellular proteins. These post-translational modifications of substrate proteins can act as molecular switches to regulate cell proliferation, activation and/or differentiation. Aberrant or excessive PK activity has been observed in many disease states including benign and malignant proliferative disorders. It is frequently possible to regulate cellular activity in vitro and in many cases to treat diseases in vivo, such as proliferative disorders, by employing PK inhibitors.

In view of the large number of protein kinase inhibitors and the multitude of proliferative and other PK-related diseases, there is an ever-existing need to provide novel classes of compounds that are useful as PK inhibitors and thus in the treatment of these Protein Tyrosine Kinase (PTK) related diseases. What is required are new classes of pharmaceutically advantageous PK inhibiting compounds.

The Philadelphia Chromosome is a hallmark for chronic myelogenous leukaemia (CML) and carries a hybrid gene that contains N-terminal exons of the BCR gene and the major C-terminal part (exons 2-11) of the ABL gene. This gene encodes a 210 kD protein, p210 Bcr-Abl, the Abl sequence of which contains the Abl tyrosine kinase domain which is tightly regulated in the wild type c-Abl, but constitutively activated in the Bcr-Abl fusion protein. This deregulated tyrosine kinase interacts with multiple cellular signalling pathways leading to transformation and deregulated proliferation of the cells (Lugo et al., Science 247, 1079 [1990]).

Mutant forms of the Bcr-Abl protein have also been identified. A detailed review of Bcr-Abl mutant forms has been published (Cowan-Jones et al, Mini Reviews in Medicinal Chemistry, 2004, 4 285-299).

GENERAL DESCRIPTION OF THE INVENTION

It has now been found that various compounds, which may be described as belonging to the naphthalene carboxylic acid and isoquinoline carboxylic acid amide class, and related compounds, can inhibit a number of protein tyrosine kinases. The compounds of Formula I described below in more detail, especially show inhibition of protein kinases e.g. protein tyrosine kinases. As examples of kinases inhibited by the compounds of the disclosure may be mentioned c-Abl and Bcr-Abl, in particular, inhibition of Bcr-Abl may be mentioned. The compounds of the present invention also inhibit mutant forms of the Bcr-Abl kinases. Other kinases which are inhibited include KDR, LCK and Ret. The disclosed compounds are appropriate for the inhibition of one or more of these and/or other receptor protein tyrosine kinases and/or the non-receptor tyrosine kinases, such as Raf, and/or for the inhibition of mutants of these enzymes. In view of these activities, the compounds can be used for the treatment of diseases related to, especially, aberrant or excessive activity of such types of kinases, especially those mentioned.

One class of target kinases of the compounds of the present invention are Bcr-Abl mutants. The mutants Glu255→Lysine, Glu255→Valine or the Thr315→Isoleucine may be especially mentioned, most especially the Thr315→Isoleucine mutant.

Other Bcr-Abl mutants include Met244→Val, Phe317→Leu, Leu248→Val, Met343→Thr, Gly250→Ala, Met351→Thr, Gly250→Glu, Glu355→Gly, Phe358→Ala, Gln252→Arg, Phe359→Val, Tyr253→His, Val379→Ale, Tyr253→Phe, Phe382→Leu, Glu255→Lys, Leu387→Met, Glu255→Val, His396→Pro, Phe311→Ile, His396→Arg, Phe311→Leu, Ser417→Tyr, Thr315→Ile, Glu459→Lys and Phe486→Ser.

DETAILED DESCRIPTION OF THE INVENTION

The invention relates to compounds of formula I

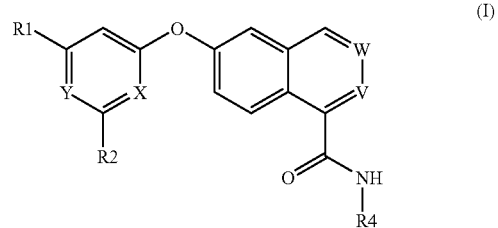

(I)

wherein

V, W, X, and Y are each independently selected from N or C—R3;

R1 and R2 are each independently selected from H, NH2, NHheteroaryl, NHCONH$_2$, NHCONH(C$_{1-7}$alkyl), NHCON(C$_{1-7}$alkyl)$_2$, NHCOR5, NHCOOR5; and R1 and R2 are not both, simultaneously, H;

R3 is hydrogen, halogen or C$_{1-7}$alkyl;

R4 is a substituted phenyl or substituted heteroaryl group including one or more nitrogen atoms, the substituted phenyl group or substituted heteroaryl group is substituted by trifluoromethyl and at least one further different substituent which is not fluoro, chloro or methyl, R5 is, independently at each occurrence, selected from $C_{1-7}$alkyl, $C_{3-7}$cycloalkyl, $C_{2-7}$alkenyl, $C_{2-7}$alkynyl, $C_{3-5}$heterocycloalkyl, aryl, heteroaryl;

or a pharmaceutically acceptable salt thereof, with the provisio that Compound of formula I is not 6-(6-Acetylamino-pyrimidin-4-yloxy)-naphthalene-1-carboxylic acid [4-(1-methyl-piperidin-4-ylmethyl)-3-trifluoromethyl-phenyl]-amide, 6-(6-Acetylamino-pyrimidin-4-yloxy)-naphthalene-1-carboxylic acid [4-(1-methyl-piperidin-4-ylidenemethyl)-3-trifluoromethyl-phenyl]-amide, 6-(6-Acetylamino-pyrimidin-4-yloxy)-naphthalene-1-carboxylic acid [4-(1-methyl-piperidin-4-yloxy)-3-trifluoromethyl-phenyl]-amide, 6-(6-Acetylamino-pyrimidin-4-yloxy)-naphthalene-1-carboxylic acid [4-(3-dimethylamino-pyrrolidin-1-yl)-3-trifluoromethyl-phenyl]-amide, 6-(6-Acetylamino-pyrimidin-4-yloxy)-naphthalene-1-carboxylic acid [4-(9-methyl-3,9-diaza-bicyclo[3.3.1]non-3-ylmethyl)-3-trifluoromethyl-phenyl]-amide, 6-(6-Acetylamino-pyrimidin-4-yloxy)-naphthalene-1-carboxylic acid [4-(4-cyclopropyl-piperazin-1-ylmethyl)-3-trifluoromethyl-phenyl]-amide, 6-(6-Acetylamino-pyrimidin-4-yloxy)-naphthalene-1-carboxylic acid [4-(1,1-dioxido-4-thiomorpholinyl)-3-trifluoromethyl-phenyl]-amide, 6-(6-Acetylamino-pyrimidin-4-yloxy)-naphthalene-1-carboxylic acid [4-[[(+/−)-3-(dimethylamino)-1-pyrrolidinyl]methyl]-3-(trifluoromethyl)phenyl]-amide, 6-(6-Acetylamino-pyrimidin-4-yloxy)-naphthalene-1-carboxylic acid [3-(4-methyl-1-piperazinyl)-5-(trifluoromethyl)phenyl]-amide, 6-(6-Acetylamino-pyrimidin-4-yloxy)-naphthalene-1-carboxylic acid [3-(4-phenylmethyl-1-piperazinyl)-5-(trifluoromethyl)phenyl]-amide, 1-[4-[[[6-(6-Acetylamino-pyrimidin-4-yloxy)-naphthalen-1yl]carbonyl]-amino]-2-(trifluoromethyl)phenyl]-3-piperidinyl]-carbamic acid, 1,1-dimethylethyl ester, 6-(6-Acetylamino-pyrimidin-4-yloxy)-naphthalene-1-carboxylic acid [4-[(3S)-3-amino-1-piperidinyl]-3-trifluoromethyl-phenyl]-amide, 6-(6-Acetylamino-pyrimidin-4-yloxy)-naphthalene-1-carboxylic acid [4-[(3R)-3-amino-1-piperidinyl]-3-trifluoromethyl-phenyl]-amide, 6-[6-(Cyclopropylcarbonyl)amino-pyrimidin-4-yloxy]-naphthalene-1-carboxylic acid [4-(1,1-dioxido-4-thiomorpholinyl)-3-trifluoromethyl-phenyl]-amide, 6-[6-(Cyclopropylcarbonyl)amino-pyrimidin-4-yloxy]-naphthalene-1-carboxylic acid [4-[(3R)-3-amino-1-piperidinyl]-3-trifluoromethylphenyl]-amide, 6-[[6-[(Cyclopropylcarbonyl)amino]-4-pyrimidinyl]oxy]-N-[4-[(4-methyl-1-piperazinyl)methyl]-3-(trifluoromethyl)phenyl]-1-naphthalenecarboxamide, 6-(6-Amino-pyrimidin-4-yloxy)-naphthalene-1-carboxylic acid [4-(4-ethyl-piperazin-1-ylmethyl)-3-trifluoromethyl-phenyl]-amide, 6-(6-Amino-pyrimidin-4-yloxy)-naphthalene-1-carboxylic acid (4-morpholin-4-yl-3-trifluoromethyl-phenyl)-amide, 6-(2-Amino-pyrimidin-4-yloxy)-isoquinoline-1-carboxylic acid [4-(4-methyl-piperazin-1-ylmethyl)-3-trifluoromethyl-phenyl]-amide, 6-(2-Acetylamino-pyrimidin-4-yloxy)-isoquinoline-1-carboxylic acid [4-(4-methyl-piperazin-1-ylmethyl)-3-trifluoromethyl-phenyl]-amide, (4-{1-[4-(4-Methyl-piperazin-1-ylmethyl)-3-trifluoromethyl-phenylcarbamoyl]-isoquinolin-6-yloxy}-pyrimidin-2-yl)-carbamic acid methyl ester, 7-(6-Amino-pyrimidin-4-yloxy)-isoquinoline-4-carboxylic acid [4-(4-methyl-piperazin-1-ylmethyl)-3-trifluoromethyl-phenyl]-amide.

In particular, the present invention relates to compounds of formula I wherein

V, W, X, and Y are each independently selected from N or C—R3;

R1 and R2 are each independently selected from H, NH2, NHCOC$_{1-7}$Alkyl, NHCOC$_{3-7}$ cyclo-Alkyl, NHCOAryl, NHCOOC$_{1-7}$Alkyl, NHCOOAryl and R1 and R2 are not both, simultaneously, H;

R3 is hydrogen, halogen or $C_{1-7}$alkyl;

R4 is a substituted phenyl or substituted heteroaryl group including one or more nitrogen atoms, the substituted phenyl group or substituted heteroaryl group is substituted by trifluoromethyl and at least one further different substituent which is not fluoro, chloro or methyl, with the provisio that Compound of formula I is not 6-(6-Acetylamino-pyrimidin-4-yloxy)-naphthalene-1-carboxylic acid [4-(1-methyl-piperidin-4-ylmethyl)-3-trifluoromethyl-phenyl]-amide, 6-(6-Acetylamino-pyrimidin-4-yloxy)-naphthalene-1-carboxylic acid [4-(1-methyl-piperidin-4-ylidenemethyl)-3-trifluoromethyl-phenyl]-amide, 6-(6-Acetylamino-pyrimidin-4-yloxy)-naphthalene-1-carboxylic acid [4-(1-methyl-piperidin-4-yloxy)-3-trifluoromethyl-phenyl]-amide, 6-(6-Acetylamino-pyrimidin-4-yloxy)-naphthalene-1-carboxylic acid [4-(3-dimethylamino-pyrrolidin-1-yl)-3-trifluoromethyl-phenyl]-amide, 6-(6-Acetylamino-pyrimidin-4-yloxy)-naphthalene-1-carboxylic acid [4-(9-methyl-3,9-diaza-bicyclo[3.3.1]non-3-ylmethyl)-3-trifluoromethyl-phenyl]-amide, 6-(6-Acetylamino-pyrimidin-4-yloxy)-naphthalene-1-carboxylic acid [4-(4-cyclopropyl-piperazin-1-ylmethyl)-3-trifluoromethyl-phenyl]-amide, 6-(6-Acetylamino-pyrimidin-4-yloxy)-naphthalene-1-carboxylic acid [4-(1,1-dioxido-4-thiomorpholinyl)-3-trifluoromethyl-phenyl]-amide, 6-(6-Acetylamino-pyrimidin-4-yloxy)-naphthalene-1-carboxylic acid [4-[[(+/−)-3-(dimethylamino)-1-pyrrolidinyl]methyl]-3-(trifluoromethyl)phenyl]-amide, 6-(6-Acetylamino-pyrimidin-4-yloxy)-naphthalene-1-carboxylic acid [3-(4-methyl-1-piperazinyl)-5-(trifluoromethyl)phenyl]-amide, 6-(6-Acetylamino-pyrimidin-4-yloxy)-naphthalene-1-carboxylic acid [3-(4-phenylmethyl-1-piperazinyl)-5-(trifluoromethyl)phenyl]-amide, 1-[4-[[[6-(6-Acetylamino-pyrimidin-4-yloxy)-naphthalen-1yl]carbonyl-]-amino]-2-(trifluoromethyl)phenyl]-3-piperidinyl]-carbamic acid, 1,1-dimethylethyl ester, 6-(6-Acetylamino-pyrimidin-4-yloxy)-naphthalene-1-carboxylic acid [4-[(3S)-3-amino-1-piperidinyl]-3-trifluoromethyl-phenyl]-amide, 6-(6-Acetylamino-pyrimidin-4-yloxy)-naphthalene-1-carboxylic acid [4-[(3R)-3-amino-1-piperidinyl]-3-trifluoromethyl-phenyl]-amide, 6-[6-(Cyclopropylcarbonyl)amino-pyrimidin-4-yloxy]-naphthalene-1-carboxylic acid [4-(1,1-dioxido-4-thiomorpholinyl)-3-trifluoromethyl-phenyl]-amide, 6-[6-(Cyclopropylcarbonyl)amino-pyrimidin-4-yloxy]-naphthalene-1-carboxylic acid [4-[(3R)-3-amino-1-piperidinyl]-3-trifluoromethylphenyl]-amide, 6-[[6-[(Cyclopropylcarbonyl)amino]-4-pyrimidinyl]oxy]-N-[4-[(4-methyl-1-piperazinyl)methyl]-3-(trifluoromethyl)phenyl]-1-naphthalenecarboxamide, 6-(6-Amino-pyrimidin-4-yloxy)-naphthalene-1-carboxylic acid [4-(4-ethyl-piperazin-1-ylmethyl)-3-trifluoromethyl-phenyl]-amide, 6-(6-Amino-pyrimidin-4-yloxy)-naphthalene-1-carboxylic acid (4-morpholin-4-yl-3-trifluoromethyl-phenyl)-amide, 6-(2-Amino-pyrimidin-4-yloxy)-isoquinoline-1-carboxylic acid [4-(4-methyl-piperazin-1-ylmethyl)-3-trifluoromethyl-phenyl]-amide, 6-(2-Acetylamino-pyrimidin-4-yloxy)-isoquinoline-1-carboxylic acid [4-(4-methyl-piperazin-1-ylmethyl)-3-trifluoromethyl-phenyl]-amide, (4-{1-[4-(4-Methyl-piperazin-1-ylmethyl)-3-trifluoromethyl-phenylcarbamoyl]-isoquinolin-6-yloxy}-pyrimidin-2-yl)-carbamic acid methyl ester, 7-(6-Amino-pyrimidin-4-yloxy)-isoquinoline-4-carboxylic acid [4-(4-methyl-piperazin-1-ylmethyl)-3-trifluoromethyl-phenyl]-amide.

More particularly, the present invention relates to compounds of formula I wherein
X, W and V are N or CH,
Y is N,
R1 and R2 are each independently selected from H, NH2, NHCOC$_{1-7}$Alkyl, NHCOC$_{3-7}$cycloAlkyl and R1 and R2 are not both, simultaneously, H;
R4 is phenyl which is substituted by trifluoromethyl and at least one further different substituent which is not fluoro, chloro or methyl, said further at least one substituent selected from Alkyl, Cyano, Halogen, HaloAlkyl, Aryl, 5- or 6-membered Heteroaryl containing one or more N, O or S atoms, such as pyridyl, indazolyl, imidazolyl, such as C$_{1-7}$Alkyl-imidazolyl, morpholinyl, thiazolyl, piperazinyl, such as piperazinyl, 4-C$_{1-7}$Alkyl-piperazinyl, C$_{1-7}$Alkyl-piperazinyl-C$_{1-7}$Alkyl, or 4-9-C$_{1-7}$Alkyl-3,9diazabicyclo3.3.1 non-9-yl-C$_{1-7}$Alkyl
or a pharmaceutically acceptable salt thereof,
with the provisio that Compound of formula I is not
6-(6-Acetylamino-pyrimidin-4-yloxy)-naphthalene-1-carboxylic acid [4-(9-methyl-3,9-diaza-bicyclo[3.3.1]non-3-ylmethyl)-3-trifluoromethyl-phenyl]-amide, 6-(6-Acetylamino-pyrimidin-4-yloxy)-naphthalene-1-carboxylic acid [4-(4-cyclopropyl-piperazin-1-ylmethyl)-3-trifluoromethyl-phenyl]-amide, 6-(6-Acetylamino-pyrimidin-4-yloxy)-naphthalene-1-carboxylic acid [3-(4-methyl-1-piperazinyl)-5-(trifluoromethyl)phenyl]-amide, 6-(6-Acetylamino-pyrimidin-4-yloxy)-naphthalene-1-carboxylic acid [3-(4-phenylmethyl-1-piperazinyl)-5-(trifluoromethyl)phenyl]-amide, 6-[[6-[(Cyclopropylcarbonyl)amino]-4-pyrimidinyl]oxy]-N-[4-[(4-methyl-1-piperazinyl)methyl]-3-(trifluoromethyl)phenyl]-1-naphthalenecarboxamide, 6-(6-Amino-pyrimidin-4-yloxy)-naphthalene-1-carboxylic acid [4-(4-ethyl-piperazin-1-ylmethyl)-3-trifluoromethyl-phenyl]-amide, 6-(6-Amino-pyrimidin-4-yloxy)-naphthalene-1-carboxylic acid (4-morpholin-4-yl-3-trifluoromethyl-phenyl)-amide, 6-(2-Amino-pyrimidin-4-yloxy)-isoquinoline-1-carboxylic acid [4-(4-methyl-piperazin-1-ylmethyl)-3-trifluoromethyl-phenyl]-amide, 6-(2-Acetylamino-pyrimidin-4-yloxy)-isoquinoline-1-carboxylic acid [4-(4-methyl-piperazin-1-ylmethyl)-3-trifluoromethyl-phenyl]-amide, (4-{1-[4-(4-Methyl-piperazin-1-ylmethyl)-3-trifluoromethyl-phenylcarbamoyl]-isoquinolin-6-yloxy}-pyrimidin-2-yl)-carbamic acid methyl ester, 7-(6-Amino-pyrimidin-4-yloxy)-isoquinoline-4-carboxylic acid [4-(4-methyl-piperazin-1-ylmethyl)-3-trifluoromethyl-phenyl]-amide.

In one embodiment, the present invention relates to compound of formula I wherein
X, W and V are N or CH,
Y is N,
R1 and R2 are each independently selected from H, NH2, NHCOC$_{1-7}$Alkyl, NHCOC$_{3-7}$cycloAlkyl and R1 and R2 are not both, simultaneously, H;
R4 is phenyl which is substituted by trifluoromethyl and simultaneously by a substitutent selected from 4-C$_{1-7}$Alkyl-piperazinyl, C$_{1-7}$Alkyl-piperazinyl-C$_{1-7}$Alkyl, piperazinyl, C$_{1-7}$Alkyl-imidazolyl, 4-9-C$_{1-7}$Alkyl-3,9diazabicyclo3.3.1 non-9-yl-C$_{1-7}$Alkyl,
or a pharmaceutically acceptable salt thereof,
with the provisio that Compound of formula I is not
6-(6-Acetylamino-pyrimidin-4-yloxy)-naphthalene-1-carboxylic acid [4-(9-methyl-3,9-diaza-bicyclo[3.3.1]non-3-ylmethyl)-3-trifluoromethyl-phenyl]-amide, 6-(6-Acetylamino-pyrimidin-4-yloxy)-naphthalene-1-carboxylic acid [4-(4-cyclopropyl-piperazin-1-ylmethyl)-3-trifluoromethyl-phenyl]-amide, 6-(6-Acetylamino-pyrimidin-4-yloxy)-naphthalene-1-carboxylic acid [3-(4-methyl-1-piperazinyl)-5-(trifluoromethyl)phenyl]-amide, 6-(6-Acetylamino-pyrimidin-4-yloxy)-naphthalene-1-carboxylic acid [3-(4-phenylmethyl-1-piperazinyl)-5-(trifluoromethyl)phenyl]-amide, 6-[[6-[(Cyclopropylcarbonyl)amino]-4-pyrimidinyl]oxy]-N-[4-[(4-methyl-1-piperazinyl)methyl]-3-(trifluoromethyl)phenyl]-1-naphthalenecarboxamide, 6-(6-Amino-pyrimidin-4-yloxy)-naphthalene-1-carboxylic acid [4-(4-ethyl-piperazin-1-ylmethyl)-3-trifluoromethyl-phenyl]-amide, 6-(6-Amino-pyrimidin-4-yloxy)-naphthalene-1-carboxylic acid (4-morpholin-4-yl-3-trifluoromethyl-phenyl)-amide, 6-(2-Amino-pyrimidin-4-yloxy)-isoquinoline-1-carboxylic acid [4-(4-methyl-piperazin-1-ylmethyl)-3-trifluoromethyl-phenyl]-amide, 6-(2-Acetylamino-pyrimidin-4-yloxy)-isoquinoline-1-carboxylic acid [4-(4-methyl-piperazin-1-ylmethyl)-3-trifluoromethyl-phenyl]-amide, (4-{1-[4-(4-Methyl-piperazin-1-ylmethyl)-3-trifluoromethyl-phenylcarbamoyl]-isoquinolin-6-yloxy}-pyrimidin-2-yl)-carbamic acid methyl ester, 7-(6-Amino-pyrimidin-4-yloxy)-isoquinoline-4-carboxylic acid [4-(4-methyl-piperazin-1-ylmethyl)-3-trifluoromethyl-phenyl]-amide.

In another embodiment, compounds of the present invention according to formula I are provided wherein, Y and X are both N and R2 is H.

A further embodiment of the present invention includes compounds of formula I in which Y is N and X is CH.

Further embodiments include compounds of formula I in which R4 is disubstituted phenyl, particularly 3,5-disubstituted phenyl, especially when Y is N and X is CH or when Y and X are both N.

Further embodiments include compounds of formula I in which W and V are both simultaneously C—R3, with R3 defined as herein above, particularly when R3 is H.

A further embodiment of the present invention includes compounds of formula I in which R4 is phenyl disubstituted with trifluoromethyl and mono- or di-C$_{1-7}$Alkyl-imadazolyl.

The following compounds are particularly preferred:

6-(2-Acetylamino-pyridin-4-yloxy)-naphthalene-1-carboxylic acid [3-(4-methyl-1H-imidazol-1-yl)-5-(trifluoromethylphenyl)]amide, 6-(2-(Cyclopropylcarbonyl)amino-pyridin-4-yloxy)-naphthalene-1-carboxylic acid [3-(4-methyl-1H-imidazol-1-yl)-5-(trifluoromethylphenyl)]amide, 6-[[2-(2,2-Dimethylpropylcarbonyl)amino-pyridin-4-yl]oxy]-naphthalene-1-carboxylic acid [3-(4-methyl-1H-imidazol-1-yl)-5-(trifluoromethylphenyl)]amide, 6-[[2-(2-Hydroxy-2-methylpropylcarbonyl)amino-pyridin-4-yl]oxy]-naphthalene-1-carboxylic acid [3-(4-methyl-1H-imidazol-1-yl)-5-(trifluoromethylphenyl)]amide, 6-[[2-[[(diethylamino)carbonyl]amino]-pyridin-4-yl]oxy]-naphthalene-1-carboxylic acid [3-(4-methyl-1H-imidazol-1-yl)-5-(trifluoromethylphenyl)]amide, 6-[[2-[(2-Pyridinyl)amino]-4-pyridinyl]oxy]-naphthalene-1-carboxylic acid [3-(4-methyl-1H-imidazol-1-yl)-5-(trifluoromethylphenyl)]amide, 6-[2-(Cyclopropylcarbonyl)amino-pyridin-4-yloxy]-naphthalene-1-carboxylic acid [4-[(4-methyl-1-piperazinyl)methyl]-3-trifluoromethyl-phenyl]amide, 6-(2-Acetylamino-pyridin-4-yloxy)-naphthalene-1-carboxylic acid [4-[(4-methyl-1-piperazinyl)methyl]-3-trifluoromethyl-phenyl]amide, 6-[4-[[[5-[[2-[(Cyclopropylcarbonyl)amino]-4-pyridinyl]oxy]-1-naphthalenyl]carbonyl]amino]-2-(trifluoromethyl)phenyl]-1-piperazinecarboxylic acid, phenylmethyl ester, 6-[[2-(Cyclopropanecarbonyl-amino)-pyridin-4-yl]oxy]-naphthalene-1-carboxylic acid (3-piperazin-1-yl-5-trifluoromethyl-phenyl)-amide, 6-][[2-(Cyclopropanecarbonyl-amino)-pyridin-4-yl]oxy]-naphthalene-1-carboxylic acid [4-(9-methyl-3,9-diaza-bicyclo[3.3.1]non-3-ylmethyl)-3-trifluoromethyl-phenyl]-amide, 6-[[2-(Cyclopropylcarbonyl)amino-pyridin-4-yl]oxy]-naphthalene-1-carboxylic acid [3-(1-methyl-1H-imidazol-1-yl)-5-(trifluoromethyl-phenyl)]-amide, 6-[[2-(Cyclopropylcarbonyl)amino-pyridin-4-yl]oxy]-naphthalene-1-carboxylic acid [3-(1,2-dimethyl-1H-imidazol-1-yl)-5-(trifluoromethylphenyl)]amide, 6-[[2-(Cyclopropylcarbonyl)amino-pyridin-4-yl]oxy]-naphthalene-1-carboxylic acid [3-[1-(phenylmethyl)-2-dimethyl-1H-imidazol-1-yl]-5-(trifluoromethylphenyl)]amide, 6-[[2-(Cyclopropylcarbonyl)amino-pyridin-4-yl]oxy]-naphthalene-1-carboxylic acid [3-(2-methyl-1H-imidazol-1-yl)-5-(trifluoromethylphenyl)]amide, 6-[[6-(Amino)-4-pyrimidinyl]oxy]-N-[4-[(4-methyl-1-piperazinyl)methyl]-3-(trifluoromethyl)phenyl]-1-naphthalenecarboxamide, 6-[[2-(Cyclopropylcarbonyl)amino-pyridin-4-yl]oxy]-isoquinoline-1-carboxylic acid [3-(4-methyl-1H-imidazol-1-yl)-5-(trifluoromethylphenyl)]amide, 6-[[2-(Cyclopropylcarbonyl)amino-pyridin-4-yl]oxy]-isoquinoline-1-carboxylic acid [3-(1-methyl-1H-imidazol-1-yl)-5-(trifluoromethylphenyl)]amide, 6-(6-Acetylamino-pyrimidin-4-yloxy)-naphthalene-1-carboxylic acid [3-(4-methyl-imidazol-1-yl)-5-trifluoromethyl-phenyl]-amide, 6-[6-(Cyclopropanecarbonyl-amino)-pyrimidin-4-yloxy]-naphthalene-1-carboxylic acid [3-(4-methyl-imidazol-1-yl)-5-(trifluoromethyl-phenyl)]-amide, 6-(6-Acetylamino-pyrimidin-4-yloxy)-isoquinoline-1-carboxylic acid [4-(4-methyl-piperazin-1-ylmethyl)-3-trifluoromethyl-phenyl]-amide, 6-(6-Amino-pyrimidin-4-yloxy)-naphthalene-1-carboxylic acid [4-(4-methyl-piperazin-1-ylmethyl)-3-trifluoromethyl-phenyl]-amide, 7-(6-Acetylamino-pyrimidin-4-yloxy)-isoquinoline-4-carboxylic acid [4-(4-methyl-piperazin-1-ylmethyl)-3-trifluoromethyl-phenyl]-amide, 6-(6-Amino-pyrimidin-4-yloxy)-naphthalene-1-carboxylic acid [3-(4-methyl-imidazol-1-yl)-5-trifluoromethyl-phenyl]-amide, 6-[(6-Amino-pyridin-4-yl)oxy]-naphthalene-1-carboxylic acid [3-(4-methyl-imidazol-1-yl)-5-trifluoromethyl-phenyl]-amide, 6-[2-(Cyclopropanecarbonyl-amino)-pyridin-4-yloxy]-naphthalene-1-carboxylic acid [4-(9-methyl-3,9-diaza-bicyclo[3.3.1]non-3-ylmethyl)-3-trifluoromethyl-phenyl]-amide, 6-[2-(Cyclopropanecarbonyl-amino)-pyridin-4-yloxy]-naphthalene-1-carboxylic acid [3-(4-methyl-imidazol-1-yl)-5-trifluoromethyl-phenyl]-amide, 7-(6-Acetylamino-pyrimidin-4-yloxy)-isoquinoline-4-carboxylic acid [4-(4-methyl-piperazin-1-ylmethyl)-3-trifluoromethyl-phenyl]-amide, 6-[2-(Cyclopropanecarbonyl-amino)-pyridin-4-yloxy]-naphthalene-1-carboxylic acid (3-piperazin-1-yl-5-trifluoromethyl-phenyl)-amide, 6-[[N-[2-(4-methyl-2-thiazol)amino]-pyridin-4-yl]oxy]-naphthalene-1-carboxylic acid [3-(4-methyl-1H-imidazol-1-yl)-5-(trifluoromethylphenyl)]amide, 6-[[2-[(1H-Imidazol-2-yl)carbonyl]amino-4-pyridinyl]oxy]-naphthalene-1-carboxylic acid [3-(4-methyl-1H-imidazol-1-yl)-5-(trifluoromethylphenyl)]amide, 6-[[2-[(2S)-2-Pyrrolidinecarbonyl]amino-pyridin-4-yl]oxy]-naphthalene-1-carboxylic acid [3-(4-methyl-1H-imidazol-1-yl)-5-(trifluoromethylphenyl)]amide, 6-[2-[(2S)-[1-[(1,1-Dimethylethoxy)carbonyl]-2-pyrrolidinecarbonyl]amino-pyridin-4-yloxy]-naphthalene-1-carboxylic acid [3-(4-methyl-1H-imidazol-1-yl)-5-(trifluoromethylphenyl)]amide, or a pharmaceutically acceptable salt thereof.

The invention may be more fully appreciated by reference to the following description, including the following definitions of terms and the concluding examples. For the sake of brevity, the disclosures of the publications cited in this specification are herein incorporated by reference. As used herein, the terms "including", "containing" and "comprising" are used herein in their open, non-limiting sense.

Any formula given herein is intended to represent compounds having structures depicted by the structural formula as well as certain variations or forms. In particular, compounds of any formula given herein may have asymmetric centers and therefore exist in different enantiomeric forms. If at least one asymmetrical carbon atom is present in a compound of the formula I, such a compound may exist in optically active form or in the form of a mixture of optical isomers, e.g. in the form of a racemic mixture. All optical isomers and their mixtures, including the racemic mixtures, are part of the present invention. Thus, any given formula given herein is intended to represent a racemate, one or more enantiomeric forms, one or more diastereomeric forms, one or more atropisomeric forms, and mixtures thereof. Furthermore, certain structures may exist as geometric isomers (i.e. cis and trans isomers), as tautomers, or as atropisomers.

Any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. Various isotopically labeled compounds of the present invention, for example those into which radioactive isotopes such as $^3$H, $^{13}$C, and $^{14}$C are incorporated. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT) including drug or substrate tissue distribution assays, or in radioactive treatment of patients. In particular, an $^{18}$F or labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Definitions

The general terms used hereinbefore and hereinafter preferably have within the context of this disclosure the following meanings, unless otherwise indicated:

"Alkyl" refers to a straight-chain or branched-chain alkyl group, preferably represents a straight-chain or branched-chain $C_{1-12}$alkyl. $C_{1-7}$alkyl is preferred.

$C_{1-7}$ alkyl is preferably alkyl with from and including 1 up to and including 7 carbon atoms, preferably from and including 1, 2, 3 or 4 carbon atoms, and is linear or branched; preferably, $C_{1-7}$ alkyl is butyl, such as n-butyl, sec-butyl, isobutyl, tert-butyl, propyl, such as n-propyl or isopropyl, ethyl, methyl, n-pentyl, n-hexyl, n-heptyl, n-octyl, n-nonyl, n-decyl, n-undecyl, n-dodecyl, with particular preference given to methyl, ethyl, n-propyl, iso-propyl, n-butyl and iso-butyl.

Preferably lower alkyl is methyl.

Alkyl may be unsubstituted or substituted, i.e. optionally substituted by one or more heteroatoms, independently selected from, for example, halogen, oxygen and/or nitrogen.

Exemplary substituents include, but are not limited to hydroxy, alkoxy, halogen and amino.

An example of a substituted alkyl is trifluoromethyl.

Where the plural form is used for compounds, salts, and the like, this is taken to mean also a single compound, salt, or the like.

Cycloalkyl is preferably $C_{3-10}$-cycloalkyl, especially $C_{3-7}$cycloalkyl, such as cyclopropyl, dimethylcyclopropyl, cyclobutyl, cyclopentyl, cyclohexyl or cycloheptyl. Cycloalkyl is preferably cyclopropyl.

Heterocycloalkyl is preferably $C_{3-10}$heterocycloalkyl, especially oxetane, tetrahydrofuran, pyrrolidine or piperidine.

An aryl, which also includes heteroaryl, group is an aromatic radical. Preferably, aryl is carbocyclic and is bound to the molecule via a bond located at an aromatic ring carbon atom of the radical (or optionally bound via a linking group, such as —O— or —CH$_2$—). Preferably aryl has a ring system of not more than 16 carbon atoms and is preferably mono- bi- or tri-cyclic and may be fully or partially substituted, for example substituted by at least two substituents. Preferably, aryl is selected from phenyl, naphthyl, indenyl, azulenyl and anthryl, and is preferably in each case unsubstituted or substituted with lower alkyl, especially methyl, ethyl or n-propyl, halo (especially fluoro, chloro, bromo or iodo), halo-lower alkyl (especially trifluoromethyl), hydroxy, lower alkoxy (especially methoxy), halo-lower alkoxy (especially 2,2,2-trifluoroethoxy), amino-lower alkoxy (especially 2-aminoethoxy), lower alkyl (especially methyl or ethyl)carbamoyl, N-(hydroxy-lower alkyl)-carbamoyl (especially N-(2-hydroxyethyl)-carbamoyl) and/or sulfamoyl-substituted aryl, especially a corresponding substituted or unsubstituted phenyl. Also, heterocyclic groups can be mentioned here, as defined below.

HeteroAryl is preferably a 5- or 6-membered atom ring containing one or more N, O or S atoms, such as pyridyl, indazolyl, imidazolyl, morpholinyl, thiazolyl.

Halogen (halo) is especially fluorine, chlorine, bromine, or iodine, especially fluorine, chlorine, or bromine most especially chlorine or fluorine.

Salts are especially the pharmaceutically acceptable salts of compounds of Formula I, especially if they are forming salt-forming groups.

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethanesulfonic acid, or aromatic sulfonic acids, for example benzene-, p-toluene- or naphthalene-2-sulfonic acid. When several basic groups are present mono- or poly-acid addition salts may be formed.

Compounds having acidic groups, a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

Such salts are formed, for example, as acid addition salts, preferably with organic or inorganic acids, from compounds of Formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of Formula I have valuable pharmacological properties, as described hereinbefore and hereinafter.

Biology

KDR inhibitor can be shown as follows: the test is conducted using KDR-receptor tyrosine kinase. The detailed procedure is as follows: 30 µL kinase solution (kinase domain of KDR, (Parast et al., Biochemistry 37 (47), 16788-801 (1998)) according to the specific activity, in order to achieve an activity of 4000-6000 counts per minute (cpm) in the sample without inhibitor) in 20 mM Tris.HCl pH 7.5, poly(Glu, Tyr) 4:1 (8 µg/mL), $MnCl_2$ (1 mM) and $MgCl_2$ (10 mM) (Sigma, Buchs, Switzerland), 8 µM [$^{33}$P]-ATP (0.2 µCi/batch), 1% dimethyl sulfoxide, and 0 to 50 µM of the compound to be tested are incubated together for 10 min at room temperature. The reaction is then ended by the addition of 10 µL 0.25 M ethylenediaminetetraacetate (EDTA) pH 7. Using a multichannel dispenser (LAB SYSTEMS, USA), an aliquot of 20 µL is applied to a PVDF (polyvinyl difluoride) Immobilon P membrane (Millipore, USA), which is incorporated into a Millipore microtitre filter manifold, and connected to a vacuum. Following complete elimination of the liquid, the membrane is washed 4 times successively in a bath containing 0.5% phosphoric acid ($H_3PO_4$), incubated for 10 min each time while shaking, then mounted in a Hewlett Packard TopCount Manifold and the radioactivity measured after the addition of 10 µl Microscint® (β-scintillation counter liquid; Packard USA). $IC_{50}$ values are determined by linear regression analysis of the percentages for the inhibition of each compound in three concentrations (as a rule 0.01, 0.1, and 1 µM). Compounds of formula I in this instance have $IC_{50}$ values in the range of 0.001 µM to 20 µM, preferred compounds especially in the range of 1 nM to 500 nM.

The efficacy of the compounds of the invention as inhibitors of c-Abl, Bcr-Abl, and tyrosine kinase activity can be demonstrated as follows:

Test for activity against wild-type and mutant Abl protein tyrosine kinase:

The test, an in vitro enzyme assay, is conducted as a filter binding assay as follows: The His-tagged kinase domain of Abl is cloned and expressed in the baculovirus/Sf9 system as described by Bhat et al., J. Biol. Chem. 1997; 272:16170-16175. A protein of 37 kD (Abl kinase) is purified by a two-step procedure over a Cobalt metal chelate column followed by an anion exchange column with a yield of 1-2 mg/L of Sf9 cells. The purity of the Abl kinase is >90% as judged by SDS-PAGE after Coomassie blue staining.

Based on the optimized assay conditions for the individual kinases a specific assay set-up was chosen. The assays were prepared and incubated on a liquid handling robot system using 384-well plates. To the assay plates containing 50 nL compound or control solutions, 4.5 µL of solution A consisting of the peptide substrate and ATP in assay buffer were added. The reactions were initiated by adding 4.5 µL of solution B consisting of the respective kinase in assay buffer. The reactions were incubated for 1 hour at 30° C. in a final reaction volume of 9.05 µL. Based on a generic assay buffer (50 mM HEPES pH7.5, 1 mM DTT, 0.02% Tween20, 0.02% BSA), following components were added depending on the chosen kinase:

c-Abl: 16 nM His-cAbl, 5 µM peptide substrate (FITC-Ahx-EAIYAAPFAKKK-CONH2), 10 mM $MgCl_2$, 10 µM ATP c-Abl-T315I: 2.4 nM His-cAbl-T315I, 5 µM peptide substrate (FITC-Ahx-EAIYAAPFAKKK-CONH2), 10 mM $MgCl_2$, 10 µM ATP After incubation, the kinase reactions were stopped by the addition of 16 µL of stop solution (100 mM HEPES, 5% DMSO, 0.1% Coating reagent, 10 mM EDTA, 0.015% Brij 35). Subsequently, the assay plates were transferred to a Caliper LabChip3000 reader and the unphosphorylated substrate and the phosphorylated product were separated and quantitated in a microfluidic chip. From these data the turnover of the kinase reactions and the effects of the compounds were calculated.

Using this test system, representative compounds show $IC_{50}$ values of <5 nM (for example compounds of examples 1, 5, 7, 8, 10, 11, 19) for the inhibition of wild-type Abl catalysed phosphorylation. The compounds of the invention also inhibit T315I mutant Abl catalysed phosphorylation, with representative compounds showing $IC_{50}$ values in the range of 47-49 nM (Example 6), 36-57 nM (Example 15) and 65-68 nM (Example 25).

Test for activity against Bcr-Abl:

32D cl3 cells are obtained from the American Type Culture Collection (ATCC CRL11346) and Ba/F3 cells are obtained from the German Collection of Microorganisms and Cell Cultures (DSMZ, Braunschweig and DSMZ No. ACC 300) Palacios et al., *Nature,* 1984; 309:126 and Palacios et al., *Cell,* 1985:41:72.

The Ba/F3.p210 cells and the murine hematopoietic 32D cl3cells, (32D p210 cells) are obtained by transfecting the IL-3-dependent murine hematopoietic Ba/F3 cell and 32D cell lines with a pGD vector containing p210BCR-ABL (B2A2) cDNA (see Daley, G. Q., Baltimore, D. *Transformation of an interleukin 3-dependent hematopoietic cell line by the chronic myeloid leukemia-specific p210 BCR-ABL protein. PNAS* 1988; 85:9312-9316; Sattler M, Salgia R, Okuda K, Uemura N, Durstin M A, Pisick E, et al. *The proto-oncogene product p120CBL and the adaptor proteins CRKL and c-CRK link c-ABL, p190BCR-ABL and p210BCR-ABL to the phosphatidylinositol-3' kinase pathway. Oncogene* 1996; 12: 839-46; and Okuda K, Golub T R, Gilliland D G, Griffin J D. *p210BCR-ABL, p190BCR-ABL, and TEL/ABL activate similar signal transduction pathways in hematopoietic cell lines. Oncogene* 1996; 13:1147-52.)

The cells express the fusion Bcr-Abl protein with a constitutively active Abl kinase and proliferate growth factor independent. The cells are expanded in RPMI 1640 (AMIMED), 10% fetal calf serum (FCS), 2 mM glutamine (Gibco) ("complete medium"), and a working stock is prepared by freezing aliquots of 2×10⁶ cells per vial in freezing medium (95% FCS, 5% DMSO (SIGMA)). After thawing, the cells are used during maximally 10-12 passages for the experiments. The antibody anti-Abl SH3 domain cat. #06-466 from Upstate Biotechnology is used for the ELISA. For detection of Bcr-Abl phosphorylation, the anti-phosphotyrosine antibody Ab PY20, labelled with alkaline phosphatase (PY10(AP)) from ZYMED (cat. #03-7722) is used. As comparison and reference compound, (N-{5-[4-(4-methyl-piperazino-methyl)-benzoylamido]-2-methylphenyl}-4-(3-pyridyl)-2-pyrimidine-amine, in the form of the methane sulfonate (monomesylate) salt (STI571) (imatinib; Gleevec™ or Glivec®; Novartis Pharmaceuticals), is used. A stock solution of 10 mM is prepared in DMSO and stored at −20° C. For the cellular assays, the stock solution is diluted in complete medium in two steps (1:100 and 1:10) to yield a starting concentration of 10 µM followed by preparation of serial threefold dilutions in complete medium. No solubility problems are encountered using this procedure. The test compounds are treated analogously. For the assay, 200'000 32D-Bcr-Abl cells in 50 µl are seeded per well in 96-well round bottom tissue culture plates. 50 µL per well of serial threefold dilutions of the test compound are added to the cells in triplicates. The final concentration of the test compound range e.g. from 5 µM down to 0.01 µM. Untreated cells are used as control. The compound is incubated together with the cells for 90 min at 37° C., 5% $CO_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 µl lysis buffer (50 mM Tris/HCl, pH 7.4, 150 mM sodium chloride, 5 mM EDTA, 1 mM EGTA, 1% NP-40 (non-ionic detergent, Roche Diagnostics GmbH, Mannheim, Germany), 2 mM sodium ortho-vanadate, 1 mM phenylmethyl sulfonylfluoride, 50 µg/mL aprotinin and 80 µg/mL leupeptin) and either used immediately for the ELISA or stored frozen at −20° C. until usage. The anti-abl SH3 domain antibody is coated at 200 ng in 50 µL PBS per well to black ELISA plates (Packard HTRF-96 black plates; 6005207) overnight at 4° C. After washing 3-times with 200 µL/well PBS containing 0.05% Tween 20 (PBST) and 0.5% TopBlock (Juro, Cat. # TB 232010), residual protein binding sites are blocked with 200 µl/well PBST, 3% TopBlock for 4 h at room temperature, followed by incubation with 50 µL lysates of untreated or test compound-treated cells (20 µg total protein per well) for 3-4 h at 4° C. After washing three times, 50 µL/well PY20(AP) (Zymed) diluted to 0.5 µg/mL in blocking buffer is added and incubated overnight (4° C.). For all incubation steps, the plates are covered with plate sealers (Costar, cat. #3095). Finally, the plates are washed another three times with washing buffer and once with deionized water before addition of 90 µL/well of the AP substrate CPDStar RTU with Emerald II. The plates now sealed with Packard Top Seal™-A plate sealers (cat. #6005185) are incubated for 45 min at room temperature in the dark and luminescence is quantified by measuring counts per second (cps) with a Packard Top Count Microplate Scintillation Counter (Top Count). For the final optimized version of the ELISA, 50 µL of the lysates of the cells grown, treated and lysed in 96-well tissue culture plates, are transferred directly from these plates to the ELISA plates that are precoated with 50 ng/well of the rabbit polyclonal ant-Abl-SH3 domain AB 06-466 from Upstate. The concentration of the anti-phosphotyrosine AB PY20 (AP) can be reduced to 0.2 µg/mL. Washing, blocking and incubation with the luminescent substrate are as above. The quantification is achieved as follows: The difference between the ELISA readout (CPS) obtained for with the lysates of the untreated 32D-bcr/abl cells and the readout for the assay background (all components, but without cell lysate) is calculated and taken as 100% reflecting the constitutively phosphorylated Bcr-Abl protein present in these cells. The activity of the compound in the Bcr-Abl kinase activity is expressed as percent reduction of the Bcr-Abl phosphorylation. The values for the $IC_{50}$ are determined from the dose response curves by graphical inter- or extrapolation. The compounds of the invention here preferably show $IC_{50}$ values in the range from 1 nM to 10 µM, most preferably 1 nM to 1000 nM. For example compounds of examples 2, 10 and 12, show $IC_{50}$ values in the range of 21-179 nM, 101-370 nM and 39-157 nM, respectively.

For cellular assays, compounds are dissolved in DMSO and diluted with complete medium to yield a starting concentration of 10 µM followed by preparation of serial 3-fold dilutions in complete medium. 32D or Ba/F3 cells expressing either 'wt'-Bcr-Abl or Bcr-Abl mutants (e.g. T-315-I) were seeded at 200,000 cells in 50 µL complete medium are seeded per well in 96-well round bottom tissue culture plates. 50 µL per well of serial 3-fold dilutions of the test compound are added to the cells in triplicates. Untreated cells are used as control. The compound is incubated together with the cells for 90 min at 37° C., 5% $CO_2$, followed by centrifugation of the tissue culture plates at 1300 rpm (Beckmann GPR centrifuge) and removal of the supernatants by careful aspiration taking care not to remove any of the pelleted cells. The cell pellets are lysed by addition of 150 µL lysis buffer (50 mM Tris/HCl, pH 7.4, 150 mM sodium chloride, 5 mM EDTA, 1 mM EGTA, 1% NP-40, 2 mM sodium ortho-vanadate, 1 mM PMSF, 50 µg/mL aprotinin and 80 µg/mL leupeptin) and either used immediately for the ELISA or stored frozen in the plates at −20° C. until usage.

The rabbit polyclonal anti-Abl-SH3 domain Ab 06-466 from Upstate was coated at 50 ng in 50 µl PBS per well to black ELISA plates (Packard HTRF-96 black plates; 6005207) over night at 4° C. After washing 3 times with 200 µL/well PBS containing 0.05% Tween20 (PBST) and 0.5% TopBlock (Juro), residual protein binding sites are blocked with 200 µL/well PBST, 3% TopBlock for 4 h at room temperature followed by incubation with 50 L lysates of untreated or compound-treated cells (20 µg total protein per well) for 3-4 h at 4° C. After 3 washings, 50 µL/well anti-phosphorosine Ab PY20(AP) labeled with alkaline phosphatase (Zymed) diluted to 0.2 µg/mL in blocking buffer is added and incubated over night (4° C.). For all incubation steps the plates are covered with plate sealers (Costar). Finally, the plates are washed another three times with washing buffer and once with deionized water before addition of 90 µL/well of the AP-substrate CDPStar RTU with Emerald II. The plates, now sealed with Packard TopSeal™-A plate sealers, are incubated for 45 min at room temperature in the dark and luminescence is quantified by measuring counts per second (CPS) with a Packard Top Count Microplate Scintillation Counter (Top Count).

The difference between the ELISA-readout (CPS) obtained for with the lysates of the untreated 32D-Bcr/Abl cells and the readout for the assay-background (all components, but without cell lysate) is calculated and taken as 100% reflecting the constitutively phosphorylated Bcr-Abl protein present in these cells. The activity of the compound on the Bcr-Abl kinase activity is expressed as percent reduction of the Bcr-Abl phosphorylation. The values for the $IC_{50}$ (and $IC_{90}$) are determined from the dose response curves by graphical extrapolation.

The compounds of the invention here preferably show $IC_{50}$ values below 3000 nM for inhibition of autophosphorylation and inhibition of IL-3 independent proliferation of Bcr-Abl mutants in Ba/F3 transfected cells, in particular T315I.

On the basis of the inhibitory studies hereinbefore described, a compound of Formula I according to the invention shows therapeutic efficacy especially against disorders dependent on protein kinase, especially proliferative diseases.

The compounds of Formula I are useful according to the invention, they inhibit the protein kinase activities mentioned, especially tyrosine protein kinases mentioned above and below, can therefore be used in the treatment of protein kinase dependent diseases. Protein kinase dependent diseases are especially proliferative diseases, preferably benign or especially malignant tumours (for example carcinoma of the kidneys, liver, adrenal glands, bladder, breast, stomach, ovaries, colon, rectum, prostate, pancreas, lungs, vagina or thyroid, sarcoma, glioblastomas and numerous tumours of the neck and head, as well as leukemias). They are able to bring about the regression of tumours and to prevent the formation of tumour metastases and the growth of (also micro) metastases. In addition they can be used in epidermal hyperproliferation (e.g. psoriasis), in prostate hyperplasia, and in the treatment of neoplasias, especially of epithelial character, for example mammary carcinoma. It is also possible to use the compounds of Formula I in the treatment of diseases of the immune system insofar as several or, especially, individual tyrosine protein kinases are involved; furthermore, the compounds of Formula I can be used also in the treatment of diseases of the central or peripheral nervous system where signal transmission by at least one tyrosine protein kinase, especially selected from those mentioned specifically, is involved.

In chronic myelogeous leukemia (CML), a reciprocally balanced chromosomal translocation in hematopoietic stem cells (HSCs) produces the BCR-ABL hybrid gene. The latter encodes the oncogenic Bcr-Abl fusion protein. Whereas ABL encodes a tightly regulated protein tyrosine kinase, which plays a fundamental role in regulating cell proliferation, adherence and apoptosis, the BCR-ABL fusion gene encodes as constitutively activated kinase, which trans-forms HSCs to produce a phenotype exhibiting deregulated clonal proliferation, reduced capacity to adhere to the bone marrow stroma and a reduces apoptotic response to mutagenic stimuli, which enable it to accumulate progressively more malignant transformations. The resulting granulocytes fail to develop into mature lymphocytes and are released into the circulation, leading to a deficiency in the mature cells and increased susceptibility to infection. ATP-competitive inhibitors of Bcr-Abl have been described which prevent the kinase from activating mitogenic and anti-apoptotic pathways (e.g. P-3 kinase and STAT5), leading to the death of the BCR-ABL phenotype cells and thereby providing an effective therapy against CML. The naphthalene carboxylic acid and isoquinoline carboxylic acid amide derivatives useful according to the present invention, especially the compounds of the Formula I, as Bcr-Abl inhibitors, including mutants thereof, are thus especially appropriate for the therapy of diseases related to its over-expression, such as leukemias, e.g. CML or ALL.

There are also experiments to demonstrate the anti-tumor activity of compounds of the Formula I in vivo: The in vivo antitumor activity is tested, for example, using breast carcinoma cell lines, such as the human estrogen dependent breast carcinoma MCF-7 (ATCC: HTB22) or ZR-75-1 (ATCC: CRL1500), or the estrogen-independent breast carcinomas MDA-MB468 (ATCC: HTB132) or MDA-MB231 (ATCC: HTB26); colon carcinoma cell lines, such as the colon-carcinoma Colo 205 (ATCC: CCL222); glioblastoma cell lines, such as the glioblastomas U-87MG (ATCC: HTB14) or U-373MG (ATCC: HTB17); lung carcinoma cell lines, such as the "small cell lung carcinomas" NCI-H69 (ATCC: HTB119) or NCI-H209 (ATCC: HTB172), or the lung carcinoma NCI-H596 (ATCC: HTB178); skin tumor cell lines, such as the melanomas Hs294T (ATCC: HTB140) or A375 (ATCC: CRL1619); tumor cell lines from the genitourinary systems, such as the ovarial carcinoma NIH-Ovcar3 (ATCC: HTB161), as well as the prostate carcinomas DU145 (ATCC: HTB81) or PC-3 (ATCC: CRL1435), or the bladder carcinoma T24 (ATCC: HTB4); epithelial carcinomas, such as the epithelial carcinoma KB31; or (especially with regard to leukemias) K562 cells (American Type Culture Collection, Mannassas, Va.) or human CFU-G cells (CFU-G stands for granulocyte colony forming unit, and it represents an early but committed granulocyte forming precursor cell that circulates in the blood stream or bone marrow) each of which is transplanted into female or male Balb/c nude mice. Other cell lines include leukemic cell lines such as K-562, SUPB15, MEG01, Ku812F, MOLM-13, BaF3, CEM/0, JURKAT/0 or U87MG.

Tumors are obtained after subcutaneous injection of the respective cells (minimum $2 \times 10^6$ cells in 100 mL phosphate buffered physiological saline) into the carrier mice (e.g. 4-8 mice per cell line). The resulting tumors are passed serially through at least three subsequent transplantations before treatment is started. Tumor fragments (about 25 mg each) are injected subcutaneously into the left flank of the animals using a 13-gauge Trocar needle under Forene narcosis (Abbott, Switzerland) for implantation. Mice transplanted with estrogen-dependent tumor are, in addition, supplied with an estrogen pellet (1.0 cm of a tube with a quality appropriate for medical purposes, Dow Chemicals, with 5 mg estradiole, Sigma). The treatment is started routinely (that is at low or intermediate tumor burden), as soon as the tumor has reached an average size of 100 mm$^3$. Tumor growth is determined once, twice or thrice weekly (depending on tumor growth of the cell line) and 24 h after the last treatment by measurement of the perpendicular diameter. In case of tumors, tumor volumes are determined according to the Formula L×D×p/6 (see Evans, B. D., Smith, I. E., Shorthouse, A. J. and Millar, J. J., Brit. J. Cancer, 1982:45:466-468). The antitumor activity is expressed as T/C % (average increase of the tumor volume of treated animals divided by the average increase of tumor volume in control animals multiplied by 100). Tumor regression (%) represents the smallest mean tumor volume compared to the mean tumor volume at the beginning of the treatment. Each animal in which the tumor reaches a diameter of more than 1.5 to 2 cm$^3$ is sacrificed. Leukemia burden is assessed by examining both peripheral white blood count and weight of spleen and thymus in animals tumored with leukemia cell lines.

An exemplary (though not limiting) schedule for administration of Compounds of Formula I or a salt thereof, is daily administration, with preferably 1 to 3 daily dosages for a longer time, possibly until the disease is cured or, if only palliative treatment is achieved, for as long as required; alternatively, treatment e.g. for 5 days, and/or administration at days 1, 4 and 9, with eventual repetition after a certain time without treatment is possible. Alternatively, treatment several times a day (e.g. 2 to 5 times) or treatment by continuous administration (e.g. infusion), e.g. at the time points indicated in the last sentence, are possible. Generally, administration is orally or parenterally, preferably orally. The test compounds are preferably diluted in water or in sterile 0.9% saline.

All human tumor cell lines are obtained from the American Type Culture Collection (ATCC, Rockville, Md., USA) if not indicated otherwise and are cultivated in the suggested media with the corresponding additives (ATCC culture conditions), if not mentioned otherwise. The c-sis- and v-sis-transformed BALB/c 3T3 cells are obtained from C. Stiles (Dana Farber Cancer Institute, Boston, Mass., USA). They are cultured in "Dulbecco's modified Eagle's medium" (DMEM), that is supplemented with 10% calf serum and Hygromycin B in a concentration of 0.2 mg/mL or G418 in a concentration of 0.5 mg/ml. BALB/c AMuLV A.6R.1 cells (ATCC) are kept in DMEM, supplemented with 10% FCS.

The pharmacological activity of Compounds of the Formula I may, for example, be demonstrated in a clinical study or in a test procedure as essentially described hereinafter.

Suitable clinical studies are, for example, open label non-randomized, dose escalation studies in patients with one of the tumor diseases mentioned above. The beneficial effects on proliferative diseases can be determined directly through the results of these studies or by changes in the study design which are known as such to a person skilled in the art. The efficacy of the treatment can be determined in such studies, e.g., in case of tumors after 18 or 24 weeks by radiologic evaluation of the tumors every 6 weeks, in case of a leukemia e.g. by determination of the count of aberrant white blood cells, and by staining mononuclear cells and/or by means of determining minimum residual disease (MRD) e.g. by FACS-LPC MRD or PCR. Alternatively, a placebo-controlled, double blind study can be used in order to prove the benefits of the Compounds of formula I useful according to the invention, mentioned herein.

A compound of Formula I can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of Formula I can besides or in addition be administered especially for tumor therapy, such as leukemia therapy, in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Therapeutic agents for possible combination are especially one or more cytostatic or cytotoxic compounds, for example a chemotherapeutic agent or several selected from the group comprising indarubicin, cytarabine, interferon, hydroxyurea, bisulfan, or an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, and an inhibitor of the interaction of an SH2 domain with a phosphorylated protein. A specific example of a combination agent is (N-{5-[4-(4-methyl-piperazino-methyl)-benzoylamido]-2-methylphenyl}-4-(3-pyridyl)-2-pyrimidine-amine (imatinibl Glivec®, Gleevec™ Novartis Pharmaceuticals). Other specific examples of a combination agent with the compounds of formula I are:

nilotinib or 4-methyl-N-[3-(4-methylimidazol-1-yl)-5-(trifluoromethyl)phenyl]-3-[(4-pyridin-3-ylpyrimidin-2-yl)amino]benzamide, dasatinib or N-(2-chloro-6-methylphenyl)-2-[[6-[4-(2-hydroxyethyl)-1-piperazinyl]-2-methyl-4-pyrimidinyl]amino]-5-thiazolecarboxamide monohydrate, bosutinib of the following formula

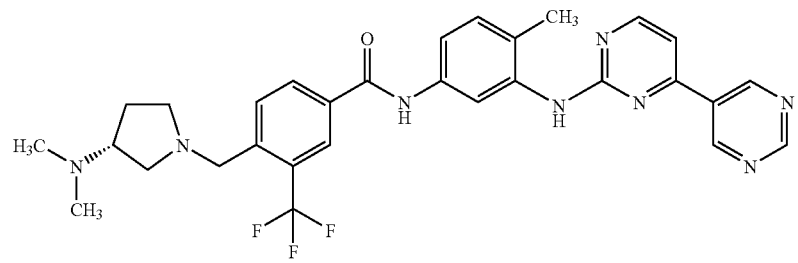

and
INNO-406 of the following formula

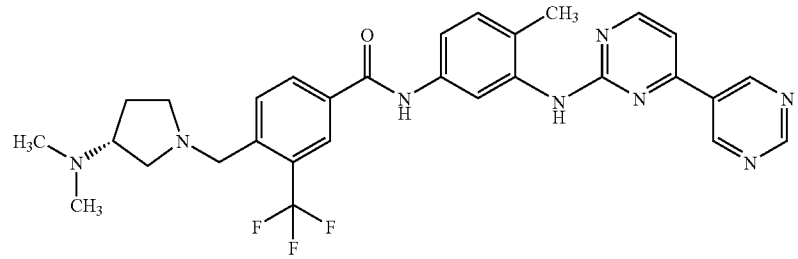

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

In general, the invention relates also to the use of a compound of Formula I for the inhibition of tyrosine kinase activity, either in vitro or in vivo.

With the groups of preferred compounds of Formula I, definitions of substituents from the general definitions mentioned hereinbefore may reasonably be used, for example, to replace more general definitions with more specific definitions or especially with definitions characterized as being preferred.

Especially, the invention relates to the use of a compound of Formula I or a possible tautomer thereof or of a pharmaceutically acceptable salt of such a compound for the preparation of a pharmaceutical composition for the treatment of a disease which responds to an inhibition of protein kinase activity, wherein the disease is a neoplastic disease. More particularly, the invention relates to the use of a compound of the Formula I or a possible tautomer thereof; or of a pharmaceutically acceptable salt of such a compound for the preparation of a pharmaceutical composition for the treatment of leukaemia which responds to an inhibition of the Abl, Abl-Bcr, including mutant forms thereof, tyrosine kinase activity.

In addition, the invention provides a method for the treatment of a disease which responds to an inhibition of protein kinase activity, which comprises administering a compound of Formula I or a pharmaceutically acceptable salt thereof, wherein the radicals and symbols have the meanings as defined above, in a quantity effective against said disease, to a warm-blooded animal requiring such treatment.

With the groups of preferred compounds of formula I mentioned hereinafter, definitions of substituents from the general definitions mentioned hereinbefore may reasonably be used, for example, to replace one or more up to all more general definitions with more specific definitions or especially with definitions characterized as being preferred.

Compounds of formula I are prepared analogously to methods that, for other compounds, are in principle known in the art, but are novel when applied in the manufacture of the compounds of the present invention, and are especially prepared according to the methods described herein below under 'Examples' or by analogous methods.

For example, a compound of the formula I can be prepared by reacting a) for the manufacture of a compound of the formula I and the other moieties are as defined for a compound of the formula I, a hydroxyl compound of the formula II,

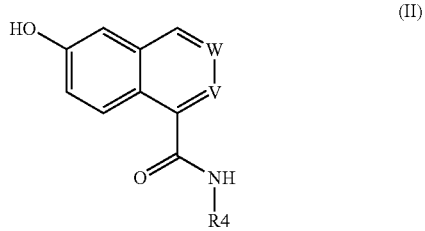

wherein
V, W and R4 have the meanings given under formula I, with a halo compound of the formula III,

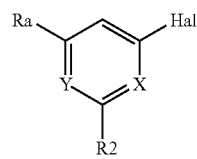

wherein R2, X, and Y are as defined for a compound of the formula I, Hal is halogen, especially chloro or bromo, and Ra is hydrogen or halo, especially chloro or bromo, and if Ra is halo reducing with hydrogen in the presence of a noble metal catalyst to hydrogen;
or
b) a carbonic acid of the formula IV,

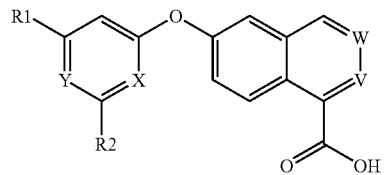

or a reactive derivative thereof, wherein
X, Y, R1, R2, W and V are as defined under formula I, with an amino compound of the formula V,

wherein W and R4 are as defined for a compound of the formula I;
and, if desired, transforming a compound of formula I into a different compound of formula I, transforming a salt of an obtainable compound of formula I into the free compound or a different salt, transforming an obtainable free compound of formula I into a salt thereof, and/or separating an obtainable mixture of isomers of a compound of formula I into individual isomers.

The reaction under a) preferably takes place in the presence of an appropriate solvent and a base, e.g. in N-methylpyrrolidine in the presence of an alkaline metal phosphate, such as potassium phosphate, for example at temperatures from 0° C. to the reflux temperature of the corresponding reaction mixture.

The reduction of halo Ra into hydrogen, if Ra is hydrogen, then subsequently takes place e.g. by hydrogenation in the presence of a noble metal catalyst, such as palladium or platinum, preferably on a carrier, such as coal, in an appropriate solvent, such as water, tetrahydrofurane or mixtures thereof, and a tertiary nitrogen base, such as tri-lower alkylamine, e.g. triethylamine, for example at temperatures from 0° C. to the reflux temperature of the corresponding reaction mixture.

The amide bond formation under b) preferably takes place, if the reactive derivative of the carbonic acid of the formula IV is a lower alkyl ester (with CO—O-lower alkyl instead of the carboxy group), e.g. by Lewis acid mediated N-acylation by first adding a Lewis acid, especially a tri-lower alkylaluminium, such as trimethylaluminium, to the amine of the formula V, e.g. in an appropriate solvent such as toluene, e.g. at temperatures from 0 to 30° C., and then adding the lower alkyl ester of the formula IV, if desired, in another solvent, such as tetrahydrofurane, and heating, e.g. to a temperature from 30 to 120° C.; or, if the reactive derivative is a carbonic acid halogenide (with a group CO-Hal, wherein Hal is halo, preferably chloro or bromo, instead of the carboxy group in formula IV; obtainable e.g. by reacting the free carbonic acid of the formula IV with oxalyl chloride in an appropriate solvent, such as methylene chloride, e.g. at temperatures in the range from 0 to 50° C.) in an appropriate solvent, such as methylene chloride, e.g. at temperatures from 0 to 50° C.; or by forming the reactive derivative of the carbonic acid of the formula IV in situ using customary condensation reagents, such as HBTU, HAT or the like.

For example, a compound of the formula I (or a corresponding precursor e.g. of the formula III or IV) wherein $R_1$ is halo (especially chloro) can be converted
(i) into the corresponding compound wherein $R_1$ is lower alkylamino by reaction with a lower alkylamine, e.g. in the presence of an appropriate solvent, such as tetrahydrofurane, e.g. at elevated temperatures, for example from 30 to 80° C.;
(ii) into the corresponding compound wherein $R_1$ is amino by reaction first with an alkaline metal azide, e.g. sodium azide, in an appropriate solvent, such as dimethylformamide, e.g. at elevated temperatures, for example from 30 to 75° C., followed by reduction, m e.g. by hydrogenation in the presence of a noble metal catalyst, such as palladium on charcoal, in an appropriate solvent, e.g. at temperatures in the range from 0 to 50° C., to the amino group;
(iii) into the corresponding compound wherein $R_1$ is lower alkoxycarbonylamino by reaction of the corresponding compound with an amino group obtainable as described under (ii) in the presence of a lower alkyl-chloroformate or the like in an appropriate solvent, e.g. methylene chloride, in the presence of a tertiary nitrogen base, e.g. pyridine, at temperatures e.g. from 0° C. to the reflux temperature of the reaction mixture;
(iv) into the corresponding compound wherein $R_1$ is lower alkylsulfonylamino (lower alkyl-S(=O)$_2$—) by reaction of the amino group obtainable as described under (ii) in the presence of a corresponding reactive lower alkylsulfonic acid derivative, e.g. an anhydride, in the presence of an appropriate solvent, e.g. methylene chloride, and a tertiary nitrogen base, e.g. pyridine, e.g. at temperatures in the range from 0 to 50° C.;
(v) into the corresponding compound wherein $R_1$ is N-lower alkylaminocarbonylamino, by reaction of the amino group obtainable as described under (ii) with a corresponding lower alkyl isocyanate in the presence of an appropriate solvent, e.g. tetrahydrofurane, preferably at elevated temperatures, e.g. from 50° C. to the reflux temperature of the reaction mixture, e.g. at 100° C.;
(vi) into the corresponding compound wherein $R_1$ is lower alkanoylamino by reaction with the corresponding lower alkanolamide in the presence of cesium carbonate, catalysts such as tris(dibenzylideneacetone)dipalladium and (9,9-dimethyl-9H-xanthene-4,5-diyl)bis[diphenyl-phosphine] and an appropriate solvent, such as dioxane, e.g. at temperatures in the range from 0 to 80° C.

A compound of the formula I wherein $R_1$ is hydroxyl can be converted into the corresponding compound wherein $R_1$ is halo, e.g. chloro, e.g. by reaction with an inorganic acid halide, e.g. PO(Hal)$_3$ wherein Hal is halo, especially chloro, in an appropriate solvent, such as acetonitrile, in the presence of a corresponding tetra-(lower alkyl)ammonium halogenide and a tertiary nitrogen base, e.g. N,N-dimethylaniline, at elevated temperatures, e.g. from 30 to 80° C. The corresponding halo compound can then be further converted as described in the preceding paragraph.

The starting materials used in the preparation of the compounds of formula I are known, capable of being prepared according to known processes, or commercially obtainable. In particular, the anilines to be used as starting material in the preparation of the compounds of formula I can be prepared as described in WO 03/099771, WO 05/051366 or in the examples of the present invention or by analogy thereto, are commercially available or can be prepared according to known processes. Starting materials and appropriate manufacturing methods can also be deduced from WO2006/059234 which is here, especially regarding such materials and manufacturing methods, incorporated by reference, as well as from the reference examples.

Compounds of the formula III and/or V can be prepared by methods as described in the examples or in analogy thereto.
General Process Conditions The following applies in general to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula IA is designated a "protecting group", unless the context indicates otherwise. The protection of functional groups by such protecting groups, the protecting groups themselves, and the reactions appropriate for their removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide and Derivate" (*Chemistry of Carbohydrates: Monosaccharides and Derivatives*), Georg Thieme Verlag, Stuttgart 1974.

A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the H$^+$ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula IA described as being preferred. The invention also relates to novel intermediates and/or starting materials. Special preference is given to reaction conditions and novel intermediates that are identical or analogous to those mentioned in the Examples.

Pharmaceutical Preparations, Methods, and Uses

The present invention relates also to pharmaceutical compositions that comprise a compound of Formula I as active ingredient and that can be used especially in the treatment of the aforementioned diseases.

The pharmacologically acceptable compounds of the present invention may be used, for example, for the preparation of pharmaceutical compositions that comprise a pharmaceutically effective amount of a compound of the Formula I or a pharmaceutically acceptable salt thereof, as active ingredient together or in admixture with a significant amount of one or more inorganic or organic, solid or liquid, pharmaceutically acceptable carriers.

The invention relates also to a pharmaceutical composition that is suitable for administration to a warm-blooded animal, especially a human (or to cells or cell lines derived from a warm-blooded animal, especially a human, e.g. lymphocytes), for the treatment or, in a broader aspect of the invention, prevention or prophylaxis against a disease that responds to inhibition of tyrosin protein kinase activity, especially one of the diseases mentioned above as being preferred for use of a compound of Formula I comprising an amount of a novel compound of Formula I or a pharmaceutically acceptable salt thereof, which is effective for said inhibition, together with at least one pharmaceutically acceptable carrier.

Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of Formula I or a pharmaceutically acceptable salt, or a hydrate or solvate thereof, and at least one pharmaceutically acceptable carrier.

The invention relates also to pharmaceutical compositions for use in a method for the prophylactic or especially therapeutic management of the human or animal body, to a process for the preparation thereof (especially in the form of compositions for the treatment of tumors) and to a method of treating tumor diseases, especially those mentioned hereinabove.

The invention relates also to processes and to the use of compounds of Formula I for the preparation of pharmaceutical preparations which comprise compounds of Formula I as active component (active ingredient).

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, sprays, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents or solubilizers, such as sodium carboxymethylcellulose, carboxymethylcellulose, dextran, polyvinylpyrrolidone or gelatin.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it being possible also for stabilisers and/or antibacterial agents to be added. Dyes or pigments may be added to the tablets or dragée coatings or the capsule casings, for example for identification purposes or to indicate different doses of active ingredient.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations.

Pharmaceutical compositions for oral administration also include hard capsules consisting of gelatin, and also soft, sealed capsules consisting of gelatin and a plasticizer. The hard capsules may contain the active ingredient in the form of granules, for example in admixture with fillers, binders, and/or glidants, and optionally stabilizers. In soft capsules, the active ingredient is preferably dissolved or suspended in suitable liquid excipients, to which stabilizers and detergents may also be added.

The invention relates likewise to a process or a method for the treatment of one of the pathological conditions mentioned hereinabove, especially a disease which responds to an inhibition of a tyrosine kinase, especially a corresponding neoplastic disease. The compounds of Formula I can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

The invention also provides for a method of treating a protein kinase dependent disease, comprising administering to a warm-blooded animal, for example a human, one or more cytostatic or cytotoxic compounds e.g. imatinib (Glivec®), dasatinib, bosutinib, nilotinib, INNO-406, in combination with a compound of the invention, whether at the same time, or a separate time. The term "the same time" is taken to mean in quick succession or immediately after one another.

The present invention relates especially also to the use of a compound of Formula I or a pharmaceutically acceptable salt thereof, especially a compound of Formula I which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably a disease which responds to an inhibition of a protein kinase, especially a neoplastic disease, more especially leukaemia which responds to an inhibition of the Abl tyrosine kinase.

The preferred dose quantity, composition, and preparation of pharmaceutical formulations (medicines) which are to be used in each case are described above.

The following Examples serve to illustrate the invention without limiting the scope thereof.

Commercially available solvents and chemicals are used for syntheses. Temperatures are measured in degrees Celsius. Unless otherwise indicated, the reactions are performed at room temperature under an inert gas atmosphere, such as argon or nitrogen. HPLC analysis are performed on a Thermo Finnigan SpectraSYSTEM instrument, UV6000 detector, detection at 216 nm, 100×4.6 mm Chromolith Performance column, RP-18e, linear solvent gradient from 2% B to 100% B in 8 min, then 2 min 100% B, 2.0 mL/min flow rate, solvents: A=0.1% aqueous formic acid and B=0.1% formic acid in acetonitrile; retention time tR given in minutes. Electrospray mass spectra are obtained with a Fisons Instruments VG Platform II. Melting points were determined on a Leitz Kofler hot-stage apparatus and are uncorrected.

EXAMPLE 1

6-[[2-(Acetylamino)-pyridin-4-yl]oxy]-naphthalene-1-carboxylic acid [3-(4-methyl-1H-imidazol-1-yl)-5-(trifluoromethylphenyl)]amide

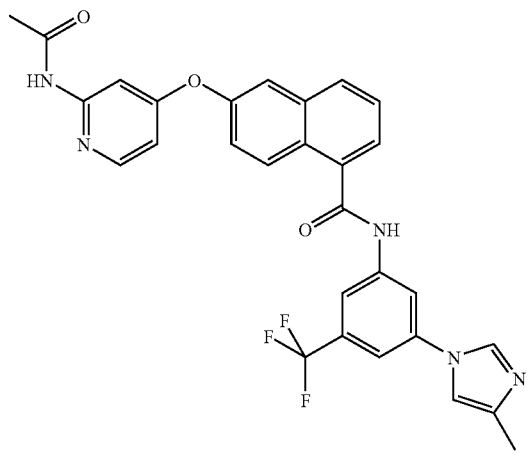

A mixture of 6-(2-chloropyridin-4-yloxy)-naphthalene-1-carboxylic acid [3-(4-methyl-1H-imidazol-1-yl)-5-(trifluoromethylphenyl)]amide (0.962 g, 1.84 mmol), acetamide (0.162 g, 2.76 mmol), $Cs_2CO_3$ (0.848 g, 2.60 mmol), 1,1'-(9,9-dimethyl-9H-xanthene-4,5-diyl)bis[1,1-diphenylphosphine (0.116 g, 0.20 mmol; xantphos; Aldrich) and $Pd_2(dba)_3$ (0.060 g, 0.066 mmol) in dioxane (20 mL) is stirred at 90° C. overnight under an argon atmosphere. The cooled mixture is treated with water (500 mL) and extracted with ethyl acetate. The combined extracts are washed (brine), dried ($Na_2SO_4$)

and the solvent is evaporated off under reduced pressure to give a crude product, which is crystallized from ethanol to give the title compound as a beige solid, m.p.: 265-270° C.

The starting material is prepared as follows:

Step 1.1: 6-(2-Chloro-pyridin-4-yloxy)-naphthalene-1-carboxylic acid [3-(4-methyl-1H-imidazol-1-yl)-5-(trifluoromethylphenyl)]amide A stirred mixture of 6-hydroxy-N-[3-(4-methyl-1H-imidazol-1-yl)-5-(trifluoromethyl)phenyl]-1-naphthalenecarboxamide (411 mg, 1.0 mmol), 2-chloro-4-nitropyridine (174 mg, 1.1 mmol) and potassium carbonate (276 mg, 2 mmol) in dimethylsulphoxide (5 mL) is heated at 55° C. for 1 h. The mixture is poured into water and the crude product is filtered off, washed with water. The crude product is dissolved in ethyl acetate, washed with brine, dried ($Na_2SO_4$) and the solvent is evaporated off under reduced pressure to give the title compound.

Step 1.2: 6-Hydroxy-N-[3-(4-methyl-1H-imidazol-1-yl)-5-(trifluoromethyl)phenyl]-1-naphthalenecarboxamide A solution of tetrabutylammonium fluoride (3.5 mL of 1 M) in tetrahydrofuran is added to a stirred solution of 6[[(1,1-dimethylethyl)diphenylsilyl]oxy]-N-[3-(4-methyl-1H-imidazol-1-yl)-5-(trifluoromethyl)phenyl]-1-naphthalenecarboxamide (1.91 g, 2.94 mmol) in tetrahydrofuran (50 mL) and the mixture is stirred at room temperature for 60 min. The solvent is evaporated off under reduced pressure and the residue is purified by column chromatography ($SiO_2$; ethyl acetate) to afford the title compound as a cream solid m.p.: 169-172° C.

Step 1.3: 6[[(1,1-Dimethylethyl)diphenylsilyl]oxy]-N-[3-(4-methyl-1H-imidazol-1-yl)-5-(trifluoromethyl)phenyl]-1-naphthalenecarboxamide Under an argon atmosphere, a stirred solution of 3-(4-methyl-1H-imidazol-1-yl)-5-(trifluoromethyl)benzenamine (0.99 g, 4.1 mmol) in dry toluene (40 mL) is treated with a solution of $AlMe_3$ (5 mL of 2 M in toluene; 10 mmol) at 40° C. After 45 min, a solution of 6[[(1,1-dimethylethyl)diphenylsilyl]oxy]-1-naphthalenecarboxylic acid, methyl ester (1.64 g, 3.72 mmol) in dry toluene (15 mL) is added and the stirred mixture is heated at 100° C. for 90 min. The cooled mixture is then added to a saturated aqueous solution of $NH_4Cl$ and stirred for 30 min. The organic phase is separated, washed with brine, dried ($Na_2SO4$) and solvent is evaporated off under reduced pressure to give a residue, which is purified by column chromatography ($SiO_2$; hexane/ethyl acetate 1:1) to afford the title compound as a beige solid.

Step 1.4: 6[[(1,1-Dimethylethyl)diphenylsilyl]oxy]-1-naphthalenecarboxylic acid, methyl ester A mixture of 6-hydroxy-1-naphthalenecarboxylic acid, methyl ester (1.01 g, 5 mmol), triethylamine (1.55 mL, 6 mmol) and N,N-dimethyl-4-pyridineamine (0.30 g, 2.5 mmol) in $CH_2Cl_2$ (25 mL) is treated with a solution of chloro(1,1-dimethylethyl)diphenylsilane (1.55 mL, 6 mmol) in $CH_2Cl_2$ (10 mL) and stirred at room temperature overnight. The mixture is washed with saturated aqueous $NaHCO_3$, dried ($Na_2SO4$) and solvent is evaporated off under reduced pressure to give a residue, which is purified by column chromatography ($SiO_2$; hexane/$CH_2Cl_2$ 1:1) to afford the title compound as an oil.

The following compounds are prepared analogously:

EXAMPLE 2

6-[[2-(Cyclopropylcarbonyl)amino-pyridin-4-yl]oxy]-naphthalene-1-carboxylic acid [3-(4-methyl-1H-imidazol-1-yl)-5-(trifluoromethylphenyl)]amide utilising cyclopropanecarboxamide in lieu of acetamide, to afford the title compound as a beige solid, m.p.: 242-244° C.

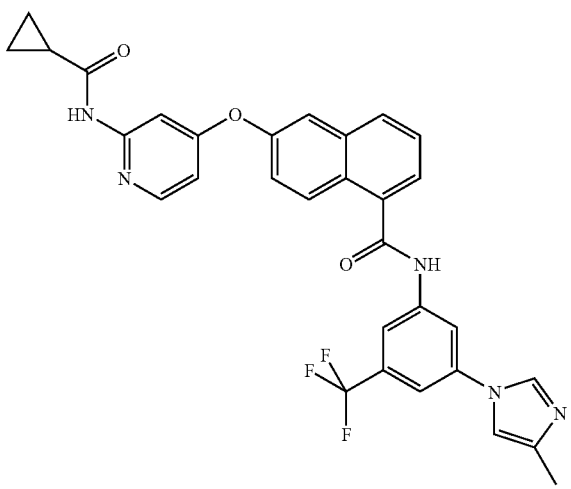

EXAMPLE 3

6-[[2-(2,2-Dimethylpropylcarbonyl)amino-pyridin-4-yl]oxy]-naphthalene-1-carboxylic acid [3-(4-methyl-1H-imidazol-1-yl)-5-(trifluoromethylphenyl)]amide utilising 2,2-dimethylpropanamide in lieu of acetamide, to afford the title compound as an amorphous beige solid, m.p.: >120° C.

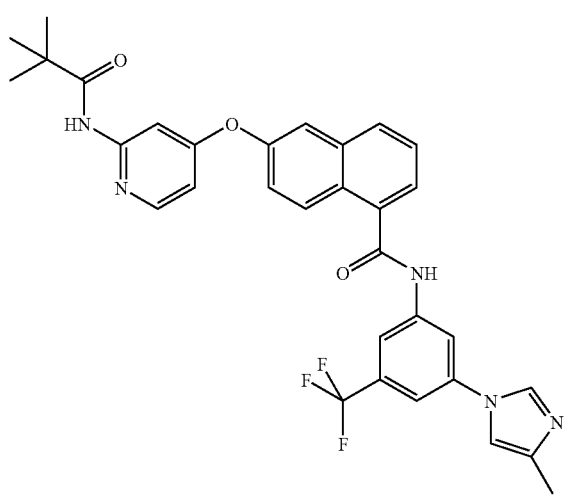

EXAMPLE 4

6-[[2-(2-Hydroxy-2-methylpropylcarbonyl)amino-pyridin-4-yl]oxy]-naphthalene-1-carboxylic acid [3-(4-methyl-1H-imidazol-1-yl)-5-(trifluoromethylphenyl)]amide utilising 2-hydroxy-2-methylpropanamide in lieu of acetamide, to afford the title compound as a beige solid, m.p.: 248-251° C.

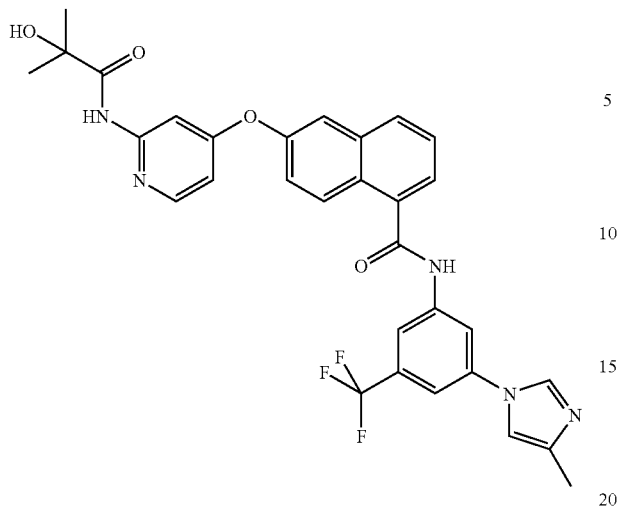

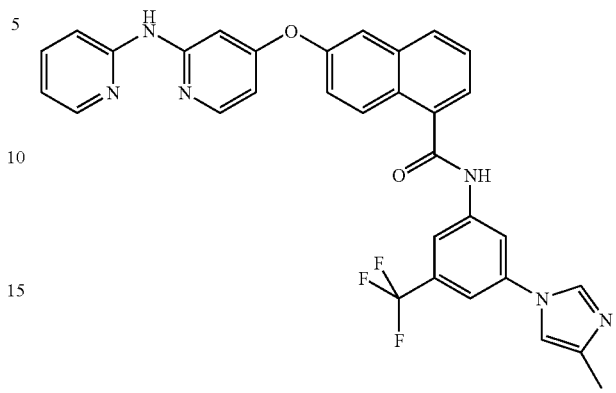

EXAMPLE 5

6-[[2-[[(diethylamino)carbonyl]amino]-pyridin-4-yl]oxy]-naphthalene-1-carboxylic acid [3-(4-methyl-1H-imidazol-1-yl)-5-(trifluoromethylphenyl)]amide utilising N,N-dimethylurea in lieu of acetamide, to afford the title compound as an amorphous beige solid, m.p.: >138° C.

EXAMPLE 7

6-[[2-(Acetylamino)-pyridin-4-yl]oxy]-naphthalene-1-carboxylic acid [4-[(4-methyl-1-piperazinyl)methyl]-3-trifluoromethyl-phenyl]amide utilising 4-[(4-methyl-1-piperazinyl)methyl]-3-(trifluoromethyl)benzenamine, in lieu of 3-(4-methyl-1H-imidazol-1-yl)-5-(trifluoromethyl)-benzenamine, to afford the title compound as a beige solid, m.p.: 112-114° C.

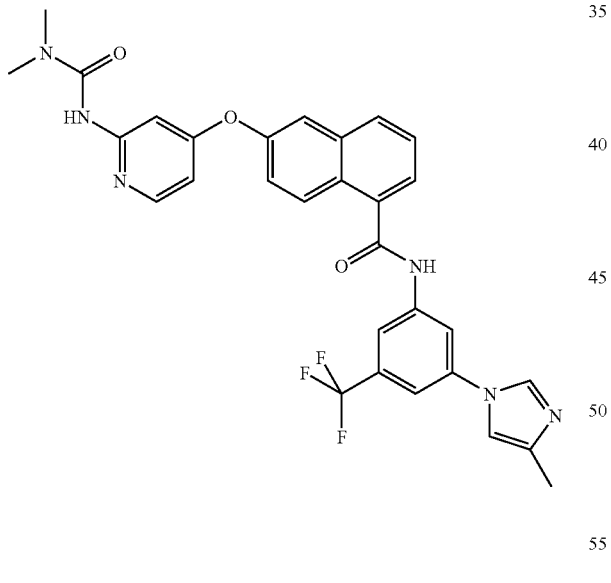

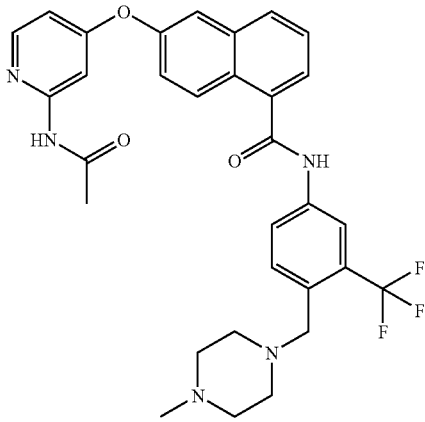

EXAMPLE 6

6-[[2-[(2-Pyridinyl)amino]-4-pyridinyl]oxy]-naphthalene-1-carboxylic acid [3-(4-methyl-1H-imidazol-1-yl)-5-(trifluoromethylphenyl)]amide utilising 2-aminopyridine in lieu of acetamide, to afford the title compound as a beige solid, m.p.: 204-206° C.

EXAMPLE 8

6-[[2-(Cyclopropylcarbonyl)amino-pyridin-4-yl]oxy]-naphthalene-1-carboxylic acid [4-[(4-methyl-1-piperazinyl)methyl]-3-trifluoromethyl-phenyl]amide

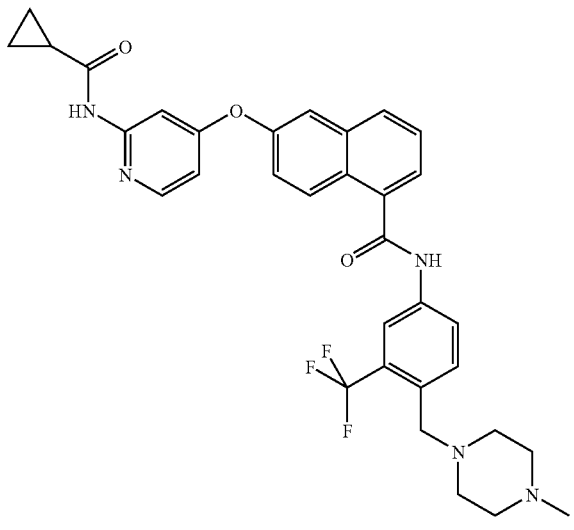

Under an argon atmosphere, a stirred solution of 4-[(4-methyl-1-piperazinyl)methyl]-3-(trifluoromethyl)benzenamine (0.131 g, 0.48 mmol) in dry toluene (5 mL) is treated with a solution of AlMe₃ (0.6 mL of 2 M in toluene; 1.1 mmol) at 18° C. After 30 min, a solution of 3-[[2-[(cyclopropylcarbonyl)amino]-4-pyridinyl]oxy]-1-naphthalenecarboxylic acid, methyl ester (0.174 g, 0.48 mmol) in toluene (5 mL) is added and the mixture is heated for 2 h at 85-95° C. The cooled mixture is then added to a saturated aqueous solution of NH₄Cl, stirred for 30 min and extracted with ethyl acetate. The combined extracts are washed (brine), dried (Na₂SO4) and solvent is evaporated off under reduced pressure to give a residue, which is purified by column chromatography (SiO₂; dichloromethane/methanol/aqueous ammonia NH₃ (d 0.88) 95:4.5:0.5) to afford the title compound as a colourless solid, m.p.: 218-220° C.

Step 8.1: 3-[[2-[(Cyclopropylcarbonyl)amino]-4-pyridinyl]oxy]-1-naphthalenecarboxylic acid, methyl ester A mixture of 3-[[2-chloro-4-pyridinyl]oxy]-1-naphthalenecarboxylic acid, methyl ester (0.188 g, 0.60 mmol), cyclopropanecarboxamide (0.077 g, 0.90 mmol), Cs₂CO₃ (0.274 g, 0.84 mmol), 1,1'-(9,9-dimethyl-9H-xanthene-4,5-diyl)bis[1,1-diphenylphosphine (0.035 g, 0.06 mmol; xantphos; Aldrich) and Pd₂(dba)₃ (0.018 g, 0.020 mmol) in dioxane (6 mL) is stirred at 90° C. for 16 h under an argon atmosphere. The cooled mixture is treated with saturated aqueous NH₄Cl (50 mL) and extracted with ethyl acetate. The combined extracts are washed (brine), dried (Na₂SO₄) and the solvent is evaporated off under reduced pressure to give a crude product, which is purified by column chromatography (SiO₂; ethylacetate/hexane 1:1) to afford the title compound as a viscous oil.

Step 8.2: 3-[[2-Chloro-4-pyridinyl]oxy]-1-naphthalenecarboxylic acid, methyl ester A stirred mixture of 6-hydroxy-1-naphthalenecarboxylic acid, methyl ester (0.202 g, 1.0 mmol), 2-chloro-4-nitropyridine (0.174 mg, 1.1 mmol) and potassium carbonate (0.276 g, 2 mmol) in dimethylsulphoxide (5 mL) is heated at 70° C. for 1 h. The mixture is poured into water and the crude product is filtered off, washed with water. The crude product is dissolved in ethyl acetate, washed with brine, dried (Na₂SO₄) and the solvent is evaporated off under reduced pressure to give a residue which is recrystallized from ethylacetate-hexane to afford the title compound as a beige crystalline solid, m.p.: 103-104° C.

EXAMPLE 9

6-[4-[[[5-[[2-[(Cyclopropylcarbonyl)amino]-4-pyridinyl]oxy]-1-naphthalenyl]carbonyl]amino]-2-(trifluoromethyl)phenyl]-1-piperazinecarboxylic acid, phenylmethyl ester is prepared utilising the method described in Example 8, but employing 4-(3-amino-5-trifluoromethyl phenyl)-1-piperazinecarboxylic acid, phenylmethyl ester in lieu of 4-[(4-methyl-1-piperazinyl)methyl]-3-(trifluoromethyl)benzenamine, to afford the title compound as a beige solid, m.p.: 227-229° C.

EXAMPLE 10

6-[[2-(Cyclopropanecarbonyl-amino)-pyridin-4-yl]oxy]-naphthalene-1-carboxylic acid (3-piperazin-1-yl-5-trifluoromethyl-phenyl)-amide A solution of 6-[4-[[[5-[[2-[(Cyclopropylcarbonyl)amino]-4-pyridinyl]oxy]-1-naphthalenyl]carbonyl]amino]-2-(trifluoromethyl)phenyl]-1-piperazinecarboxylic acid, phenylmethyl ester (Example 9; 227 mg) in a 2:1 mixture of ethanol and tetrahydrofuran (15 mL) is hydrogenated in the presence of Pd/C (45 mg of 10%; Engelhard 4505) at room temperature. After 8.5 h, when hydrogen uptake is complete, the catalyst is filtered off (hyflo), solvent is evaporated off under reduced pressure to give a residue, which is purified by column chromatography (SiO₂; CH₂Cl₂/MeOH/NH₃ (d 0.88) 90:9:1) and recrystallized from ethanol to afford the title compound as a colourless solid, m.p.: 244-247° C.

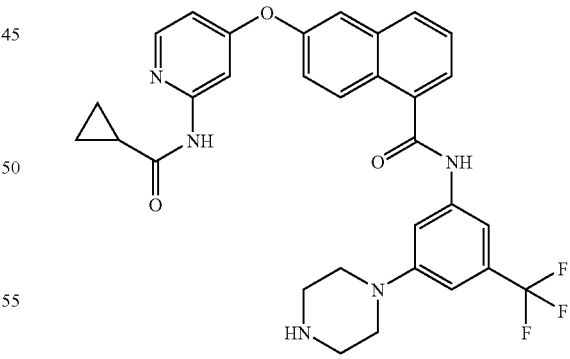

EXAMPLE 11

6-][[2-(Cyclopropanecarbonyl-amino)-pyridin-4-yl]oxy]-naphthalene-1-carboxylic acid [4-(9-methyl-3,9-diaza-bicyclo[3.3.1]non-3-ylmethyl)-3-trifluoromethyl-phenyl]-amide is prepared utilising the method described in Example 8, but employing 4-(9-methyl-3,9-diaza-bicyclo[3.3.1]non-3-ylmethyl)-3-(trifluoromethyl)benzenamine in lieu of 4-[(4-methyl-1-piperazinyl)methyl]-3-(trifluoromethyl)benzenamine, to afford the title compound as an amorphous pale-yellow solid, m.p.: >138° C.

3-(1,2-dimethyl-1H-imidazol-5-yl)-5-(trifluoromethyl)-benzenamine in lieu of 4-[(4-methyl-1-piperazinyl)methyl]-3-(trifluoromethyl)benzenamine, to afford the title compound as a pale-yellow solid, m.p.: 229-231° C.

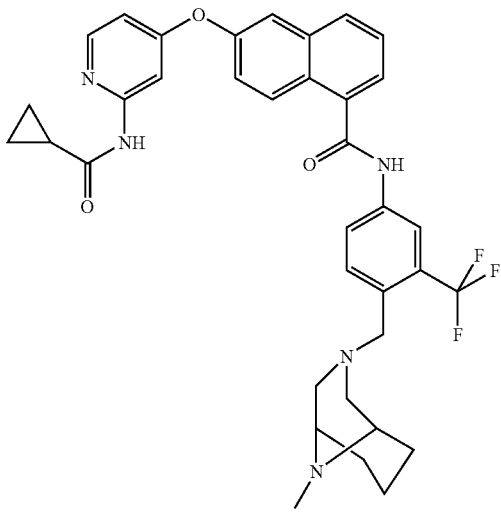

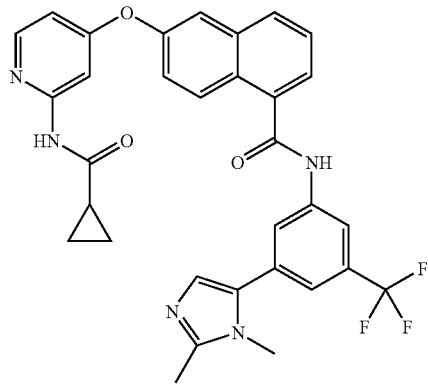

EXAMPLE 12

6-[[2-(Cyclopropylcarbonyl)amino-pyridin-4-yl]oxy]-naphthalene-1-carboxylic acid [3-(1-methyl-1H-imidazol-1-yl)-5-(trifluoromethylphenyl)]amide was prepared utilising the method described in Example 8, but employing 3-(1-methyl-1H-imidazol-5-yl)-5-(trifluoromethyl)-benzenamine in lieu of 4-[(4-methyl-1-piperazinyl)methyl]-3-(trifluoromethyl)benzenamine, to afford the title compound as a pale-yellow amorphous solid.

EXAMPLE 14

6-[[2-(Cyclopropylcarbonyl)amino-pyridin-4-yl]oxy]-naphthalene-1-carboxylic acid [3-[1-(phenylmethyl)-2-dimethyl-1H-imidazol-1-yl]-5-(trifluoromethylphenyl)]amide was prepared utilising the method described in Example 8, but employing 3-[1-(phenylmethyl)-2-methyl-1H-imidazol-5-yl]-benzenamine in lieu of 4-[(4-methyl-1-piperazinyl)methyl]-3-(trifluoromethyl)benzenamine, to afford the title compound as an amorphous pale-yellow solid, m.p.: >128° C.

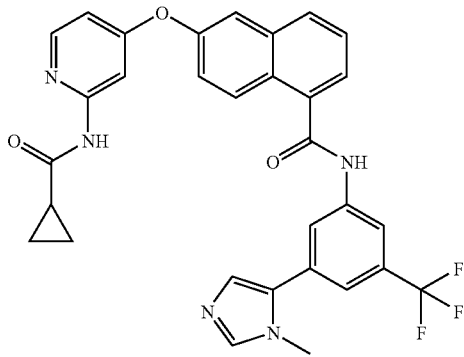

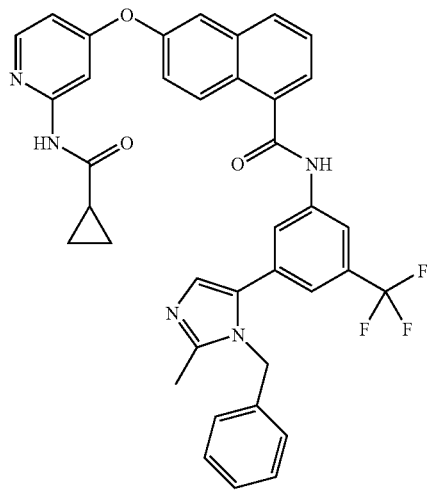

EXAMPLE 13

6-[[2-(Cyclopropylcarbonyl)amino-pyridin-4-yl]oxy]-naphthalene-1-carboxylic acid [3-(1,2-dimethyl-1H-imidazol-1-yl)-5-(trifluoromethylphenyl)]amide was prepared utilising the method described in Example 8, but employing

EXAMPLE 15

6-[[2-(Cyclopropylcarbonyl)amino-pyridin-4-yl]
oxy]-naphthalene-1-carboxylic acid [3-(2-methyl-
1H-imidazol-1-yl)-5-(trifluoromethylphenyl)]amide

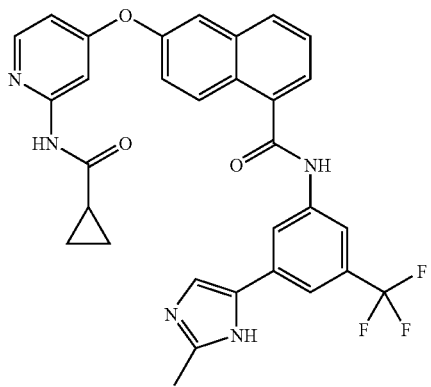

A solution of 6-[[2-(Cyclopropylcarbonyl)amino-pyridin-4-yl]oxy]-naphthalene-1-carboxylic acid [3-[1-(phenylmethyl)-2-dimethyl-1H-imidazol-1-yl]-5-(trifluoromethylphenyl)]amide (Example 14; 232 mg) in ethanol (5 mL) is hydrogenated in the presence of palladium hydroxide on carbon (40 mg; Pearlman's catalyst) at room temperature. After 12 days, the catalyst is filtered off (hyflo), solvent is evaporated off under reduced pressure to give a residue, which is purified by column chromatography (SiO$_2$; CH$_2$Cl$_2$/MeOH/NH$_3$ (d 0.88) 95:4.5:0.5) to afford the title compound as a beige solid, m.p.: 269-272° C.

EXAMPLE 16

6-[[6-(Amino)-4-pyrimidinyl]oxy]-N-[4-[(4-methyl-
1-piperazinyl)methyl]-3-(trifluoromethyl)phenyl]-1-
naphthalenecarboxamide

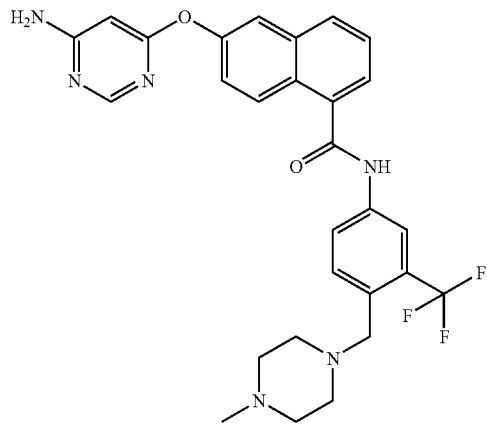

A solution containing ~50% of propylphosphonic anhydride in N,N-dimethylformamide (Fluka; 700 μL, ~1.1 mmol) is added to a stirred mixture of 6-[(6-amino-4-pyrimidinyl)oxy]-1-naphthalenecarboxylic acid (200 mg, 0.71 mmol), 4-[(4-methyl-1-piperazinyl)methyl]benzeneamine (194 mg, 0.71 mmol) and triethylamine (812 μL, 6 mmol) in 10 mL N,N-dimethylformamide. After stirring for 24 hours at 50° C., the mixture is treated with a saturated aqueous sodium hydrogen carbonate and extracted with ethyl acetate. The combined extracts are dried (Na$_2$SO4) and solvent is evaporated off under reduced pressure to give a residue, which is purified by column chromatography (SiO$_2$; CH$_2$Cl$_2$/MeOH/NH$_3$ (d 0.88) 90:9:1) and recrystallised from ethylacetate-hexane to afford the title compound as a pale-yellow solid, m.p.: 127-130° C.

EXAMPLE 17

6-[[2-(Cyclopropylcarbonyl)amino-pyridin-4-yl]
oxy]-isoquinoline-1-carboxylic acid [3-(4-methyl-
1H-imidazol-1-yl)-5-(trifluoromethylphenyl)]amide To a solution of 6-o[2-(cyclopropanecarbonyl-amino)-pyridin-4-yloxy]-isoquinoline-1-carboxylic acid (50 mg, 0.143 mmol) in dimethylformamide (1 mL) stirred at 20° C. is added 3-(4-methylimidazol-1-yl)-5-trifluoromethyl-phenylamine (35 mg, 0.143 mmol), 1-hydroxybenzotriazole (23 mg, 0.172 mmol), 1-ethyl-3-(3-dimethylaminopropyl)-carbodiimide (30 mg, 0.157 mmol) and diisopropylamine (62 uL, 0.357 mmol). After 18 h the reaction mixture is dissolved in ethyl acetate, washed with a saturated aqueous solution of sodium hydrogen carbonate and brine. The combined organic phases are dried (Na$_2$SO4), concentrated under reduced pressure and the residue is purified by column chromatography (ethyl acetate/hexane) to afford the title compound as an amorphous solid. MH$^+$: 572.9/571.1; HPLC t$_R$: 4.73 min.

Step 17.1: 6-[2-(Cyclopropanecarbonyl-amino)-pyridin-4-yloxy]-isoquinoline-1-carboxylic acid Cyclopropanecarboxylic acid (4-nitro-pyridin-2-yl)-amide (200 mg, 0.965 mmol), 6-hydroxy-isoquinoline-1-carboxylic acid (183 mg, 0.965 mmol), and potassium carbonate (267 mg, 1.93 mmol) are stirred in dimethylsulphoxide (10 mL) at 90° C. for 24 h. After cooling to 20° C., the dimethylsulphoxide is partially evaporated under reduced pressure, water is added, the solution is carefully acidified with trifluoroacetic acid and the resulting solution is purified using a MPLC reverse phase chromatography (Merck LiChroprep® RP-18, acetonitrile/water 0.1% trifluoroacetic acid) to afford the title compound as a solid. M-H, 348.1; HPLC t$_R$: 3.29 min.

Step 17.2: Cyclopropanecarboxylic acid (4-nitro-pyridin-2-yl)-amide

2-Chloro-4-nitro-pyridine (476 mg, 3 mmol), cyclopropanecarboxylic acid amide (306 mg, 3.6 mmol), and tripotassium phosphate (892 mg, 4.2 mmol) are mixed in dimethoxyethane under an argon atmosphere. (2'-Dicyclohexylphosphanyl-biphenyl-2-yl)-dimethyl-amine (118 mg, 0.3 mmol) and Pd2(dba)3 (275 mg, 0.3 mmol) are added and the mixture is stirred for 3 h at 90° C. Further 0.5 equivalent cyclopropanecarboxylic acid amide (128 mg, 1.5 mmol) is added and the mixture is stirred for 1 additional hour. After cooling at RT the reaction mixture is taken in ethyl acetate, washed with a solution of saturated sodium hydrogen carbonate and brine. The combined organic phases are dried (Na$_2$SO4), concentrated under reduced pressure and the residue is purified by column chromatography (ethyl acetate/hexane) to afford the title compound as a brown solid. M-H$^-$= 206.1, HPLC t$_R$: 4.62 min.

EXAMPLE 18

6-[[2-(Cyclopropylcarbonyl)amino-pyridin-4-yl]oxy]-
isoquinoline-1-carboxylic acid [3-(1-methyl-1H-imidazol-1- yl)-5-(trifluoromethylphenyl)]amide is prepared utilising the method described in Example 17, but employing 3-(3-methyl-3H-imidazol-4-0)-5-trifluoromethyl-phenylamine in lieu of 3-(4-methyl-imidazol-1-yl)-5-trifluoromethyl-phenylamine, to afford the title compound as a solid. MH+: 573.3/ 571.0; HPLC $t_R$: 4.59 min.

Step 18.1: 3-(3-Methyl-3H-imidazol-4-yl)-5-trifluoromethyl-phenylamine 3-(3-Methyl-3H-imidazol-4-yl)-5-trifluoromethyl-phenyl]-carbamic acid tert-butyl ester (900 mg, 2.64 mmol) was treated with HCl 4 N in dioxan for 1 h at RT. The reaction mixture is then dissolved in ethyl acetate, washed with a saturated aqueous solution of sodium hydrogen carbonate and with brine. The combined organic phases are dried (Na₂SO4), concentrated under reduced pressure and the residue is purified by column chromatography (ethyl acetate/aqueous ammonia 0.1%) to afford the title compound as a solid. MH+: 242.2/240.3; HPLC $t_R$: 3.21 min.

Step 18.2: 3-(3-Methyl-3H-imidazol-4-yl)-5-trifluoromethyl-phenyl]-carbamic acid tert-butyl ester To a solution of tert-butyl 3-bromo-5-(trifluoromethyl) phenylcarbamate (1.7 g) in dioxan (39 mL) is added bis(pinacolato)diboron (980 mg, 3.8 mmol), potassium acetate (1.13 g, 11.6 mmol) and Pd(dppf)Cl2×CH₂Cl₂ (315 mg, 0.386 mmol). The reaction mixture is stirred at 80° C. for 2 h. After cooling to 20° C. the reaction mixture is dissolved in ethyl acetate and washed with brine. The combined organic phases are dried (Na₂SO4), concentrated under reduced pressure. The residue is dissolved in hexane, filtered over celite and the filtrate is concentrated under reduced pressure. The obtained yellowish oily residue is dissolved in dimethoxyethane (38 mL), and to this solution are added 5-bromo-1-methyl-1H-imidazole (367 mg, 2.28 mmol), potassium carbonate (5.13 mL 2 M solution), dichloro-bis(triphenylphosphine)palladium (II) (267 mg, 0.38 mmol). The mixture is stirred for 4 h at 80° C. under argon atmosphere. After cooling to 20° C. the reaction mixture is dissolved in ethyl acetate, washed with a solution of saturated sodium hydrogen carbonate and with brine. The combined organic phases are dried (Na₂SO4), concentrated under reduced pressure and the residue is purified by column chromatography (methanol/dichloromethane) to afford the title compound as an oil. MH+=342.2/340.2, HPLC $t_R$: 4.25 min.

EXAMPLE 19

6-[[6-(Acetylamino)-pyrimidin-4-yl]oxy]-naphthalene-1-carboxylic acid [3-(4-methyl-imidazol-1-yl)-5-trifluoromethyl-phenyl]-amide Anhydrous tripotassium phosphate (848 mg, 4.0 mmol) is added to a stirred solution of 6-hydroxy-N-[3-(4-methyl-1H-imidazol-1-yl)-5-(trifluoromethyl)phenyl]-1-naphthalenecarboxamide (411 mg, 1.0 mmol) in toluene (40 mL) under an argon atmosphere at 110° C. N-(6-Chloro-4-pyrimidinyl)-acetamide (252 mg, 1.5 mmol) is added and the mixture is stirred at 110° C. for a further 50 hours. The solvent is evaporated off under reduced pressure and the residue is washed with a saturated aqueous solution of NH₄Cl and dried. The crude product is purified by recrystallisation from methanol to afford the title compound as a beige solid, m.p.: 291-293° C.

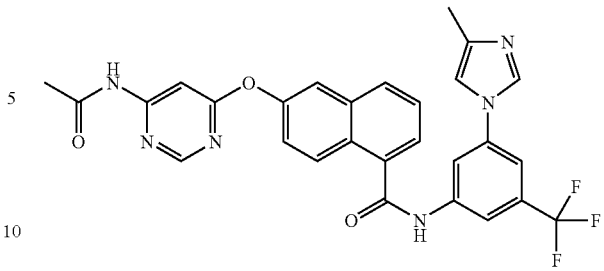

EXAMPLE 20

6-[[6-(Cyclopropanecarbonyl)amino-pyrimidin-4-yl] oxy]-naphthalene-1-carboxylic acid [3-(4-methyl-imidazol-1-yl)-5-trifluoromethyl-phenyl]-amide is prepared utilising the method described in Example 19, but employing N-(6-chloro-4-pyrimidinyl)-cyclopropanecarboxamide in lieu of N-(6-chloro-4-pyrimidinyl)-acetamide, to afford the title compound as a beige solid, m.p.: 216-220° C.

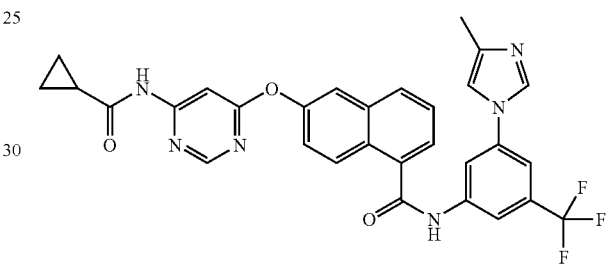

EXAMPLE 21

6-[[6-Amino-pyrimidin-4-yl]oxy]-naphthalene-1-carboxylic acid [3-(4-methyl-imidazol-1-yl)-5-trifluoromethyl-phenyl]-amide is prepared utilising the method described in Example 19, but employing 6-chloro-4-pyrimidinamine in lieu of N-(6-chloro-4-pyrimidinyl)-acetamide, to afford the title compound as an amorphous beige solid, m.p.: >148° C.

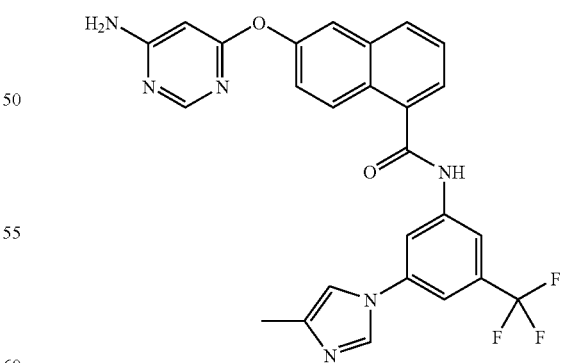

EXAMPLE 22

6-[[N-[2-(4-methyl-2-thiazolyl)amino]-pyridin-4-yl] oxy]-naphthalene-1-carboxylic acid [3-(4-methyl-1H-imidazol-1-yl)-5-(trifluoromethylphenyl)]amide is prepared utilising the method described in Example 19, but employing 4-nitro-N-2-thiazolyl-2-pyridinamine in lieu of N-(6-chloro-4-pyrimidinyl)-acetamide, to afford the title compound as a beige solid, m.p.: 277-282° C.

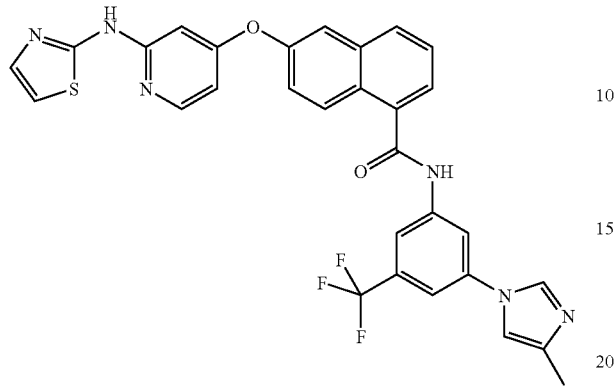

Step 22.1: 4-Nitro-N-2-thiazolyl-2-pyridinamine

A mixture of 2-chloro-nitropyridine (80 mg, 0.5 mmol), 2-aminothiazole (62 mg, 0.6 mmol), $Na_2CO_3$ (74 mg, 0.7 mmol), 1,1'-(9,9-dimethyl-9H-xanthene-4,5-diyl)bis[1,1-diphenylphosphine (17 mg, 0.03 mmol; xantphos; Aldrich) and $Pd_2(dba)_3$ (9 mg, 0.01 mmol) in dioxane (3 mL) is stirred at 90° C. for 90 min under an argon atmosphere. The cooled mixture is treated with water (500 mL) and extracted with ethyl acetate. The combined extracts are washed (brine), dried ($Na_2SO_4$) and the solvent is evaporated off under reduced pressure to give a crude product, which is purified by column chromatography ($SiO_2$; $CH_2Cl_2$/MeOH/$NH_3$ (d 0.88) 95:4.5:0.5) and recrystallized from ethanol-diethyl-ether to give the title compound as an orange crystalline solid, m.p.: 230-233° C.

EXAMPLE 23

6-[(6-Amino-pyridin-4-yl)oxy]-naphthalene-1-carboxylic acid [3-(4-methyl-imidazol-1-yl)-5-trifluoromethyl-phenyl]-amide

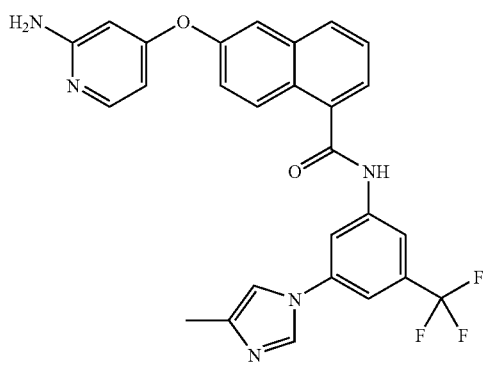

Hydrochloric acid (5 mL of 4.0 M) is added to a solution of 6-[[2-(Acetylamino)-pyridin-4-yl]oxy]-naphthalene-1-carboxylic acid [3-(4-methyl-1H-imidazol-1-yl)-5-(trifluoromethylphenyl)]amide (218 mg, 0.4 mmol; Example 1) in etha-nol (20 mL) and the mixture is stirred at 100° C. for 5 h. The cooled mixture is treated with aqueous sodium hydroxide (20 mL of 1 M) and extracted with ethyl acetate. The combined extracts are washed (brine), dried ($Na_2SO_4$) and the solvent is evaporated off under reduced pressure to give a crude product, which is crystallized from ethyl acetate to give the title compound as a beige solid, m.p.: 236-239° C.

EXAMPLE 24

6-[[2-[(1H-Imidazol-2-yl)carbonyl]amino-4-pyridinyl]oxy]-naphthalene-1-carboxylic acid [3-(4-methyl-1H-imidazol-1-yl)-5-(trifluoromethylphenyl)] amide

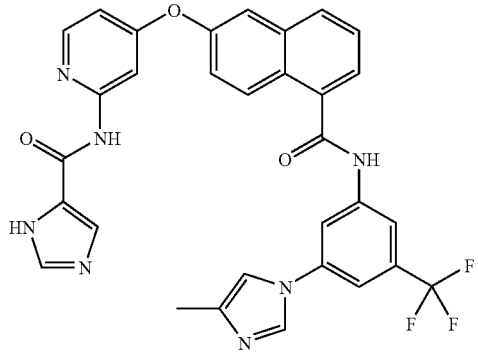

A mixture of 1-[bis(dimethylamino)methylene-1H-1,2,3-triazolo[4,5-b]pyridinium-3-oxide, hexafluorophosphate (209 mg, 0.55 mmol; HATU), imidazole-2-carboxylic acid (58 mg, 0.50 mmol) and ethyldiisopropylamine (0.256 mL, 1.5 mmol) in dimethylformamide (2.5 mL) is stirred at room temperature for 20 min. To the mixture is then added 6-[(6-Amino-pyrimidin-4-yl)oxy]-naphthalene-1-carboxylic acid [3-(4-methyl-imidazol-1-yl)-5-trifluoromethyl-phenyl]-amide (125 mg, 0.25 mmol) and the mixture is stirred at 60° C. for 21 h. The cooled mixture is treated with saturated aqueous sodium hydrogen carbonate and the crude product is separated by filtration and purified by column chromatography ($SiO_2$; $CH_2Cl_2$/EtOH 9:1) to give the title compound as an beige solid, m.p.: 248-252° C.

EXAMPLE 25

6-[[2-[(2S)-2-Pyrrolidinecarbonyl]amino-pyridin-4-yl]oxy]-naphthalene-1-carboxylic acid [3-(4-methyl-1H-imidazol-1-yl)-5-(trifluoromethylphenyl)]amide Trifluoroacetic acid (0.5 mL) is added to a stirred solution of (S)-2-[4-[5-[3-(4-methyl-imidazol-1-yl)-5-trifluoromethyl-phenylcarbamoyl]-naphthalen-2-yloxy]-pyridin-2-yl-carbamoyl]-pyrrolidine-1-carboxylic acid 1,1-dimethylethyl ester (33 mg, 0.047 mmol) in dichloromethane (1 mL) at 0° C. After 2 h the reaction mixture is treated with saturated aqueous sodium hydrogen carbonate (50 mL) and extracted with ethyl acetate. The combined extracts are dried ($Na_2SO_4$) and the solvent is evaporated off under reduced pressure to give a crude product, which is re-dissolved in ethyl acetate and further washed with water until the title compound precipitates as a white solid. $MH^+$=600.1, HPLC $t_R$: 3.84 min.

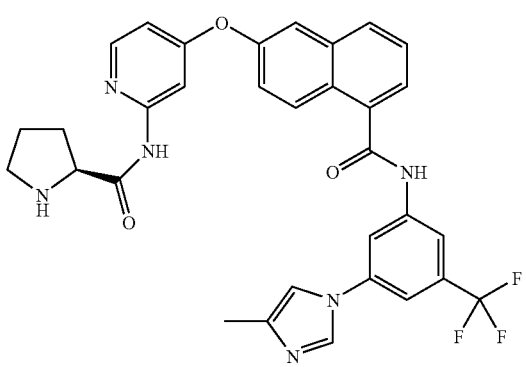

Step 25.1

6-[2-[(2S)-[1-[(1,1-Dimethylethoxy)carbonyl]-2-pyrrolidinecarbonyl]amino-pyridin-4-yloxy]-naphthalene-1-carboxylic acid [3-(4-methyl-1H-imidazol-1-yl)-5-(trifluoromethylphenyl)]amide is prepared according to the method described in Example 1, utilising 2-(aminocarbonyl)-1-pyrrolidinecarboxylic acid, 1,1-dimethylethyl ester, in lieu of acetamide, to afford the title compound as a beige solid. MH$^+$=701.2, HPLC $t_R$: 4.91 min.

The invention claimed is:
1. A compound of formula I

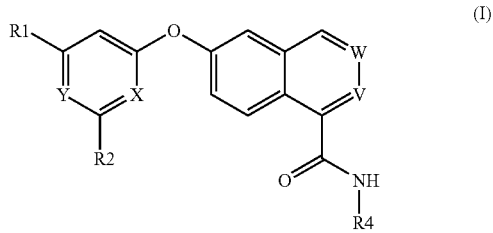

wherein
X is selected from N or CH;
$R_1$ is selected from $NH_2$, NHheteroaryl, NHCON($C_{1-7}$alkyl)$_2$, NHCOR$_5$,;
$R_4$ is a phenyl substituted by trifluoromethyl and at least one further substituent selected from imidazolyl, piperazinyl, $C_{1-7}$Alkyl-piperazinyl-$C_{1-7}$Alkyl, and 9-methyl-3,9-diazabicyclo[3.3.1]nonan-3yl; wherein said imidazolyl of $R_4$ is substituted with either 1 to 2 methyl groups or a methyl and a benzyl group;
$R_5$ is selected from $C_{1-7}$alkyl, $C_{3-7}$cycloalkyl, $C_{2-7}$alkenyl, $C_{2-7}$alkynyl, $C_{3-5}$heterocycloalkyl, aryl, heteroaryl;
or a pharmaceutically acceptable salt thereof,
with the proviso that Compound of formula I is not a compound selected from
6-(6-Acetylamino-pyrimidin-4-yloxy)-naphthalene-1-carboxylic acid [4-(9-methyl-3,9-diaza-bicyclo[3.3.1]non-3-ylmethyl)-3-trifluoromethyl-phenyl]-amide,
6-(6-Acetylamino-pyrimidin-4-yloxy)-naphthalene-1-carboxylic acid [3-(4-methyl-1-piperazinyl)-5-(trifluoromethye)phenyl]-amide,
6-[[6-[(Cyclopropylcarbonyl)amino]-4-pyrimidinyl]oxy]-N-[4-[(4-methyl-1-piperazinyl)methyl]-3-(trifluoromethyl)phenyl]-1-naphthalenecarboxamide,
6-(6-Amino-pyrimidin-4-yloxy)-naphthalene-1-carboxylic acid [4-(4-ethyl-piperazin-1-ylmethyl)-3-trifluoromethyl-phenyl]-amide, and
7-(6-Amino-pyrimidin-4-yloxy)-isoquinoline-4-carboxylic acid [4-(4-methyl-piperazin-1-ylmethyl)-3-trifluoromethyl-phenyl]-amide.

2. The compound of claim 1, wherein $R_4$ is 3,5-disubstituted phenyl.

3. The compound of claim 2, wherein $R_4$ is 3,5-disubstituted phenyl disubstituted with trifluoromethyl and mono- or di-$C_{1-7}$Alkyl-imadazolyl.

4. The compound of claim 1, selected from the group consisting of 6-(2-Acetylamino-pyridin-4-yloxy)-naphthalene-1-carboxylic acid [3-(4-methyl-1H-imidazol-1-yl)-5-(trifluoromethylphenyl)]amide,
6-(2-(Cyclopropylcarbonyl)amino-pyridin-4-yloxy)-naphthalene-1-carboxylic acid [3-(4-methyl-1H-imidazol-1-yl)-5-(trifluoromethylphenyl)]amide,
6-[[2-(2,2-Dimethylpropylcarbonyl)amino-pyridin-4-yl]oxy]-naphthalene-1-carboxylic acid [3-(4-methyl-1H-imidazol-1-yl)-5-(trifluoromethylphenyl)]amide,
6-[[2-(2-Hydroxy-2-methylpropylcarbonyl)amino-pyridin-4-yl]oxy]-naphthalene-1-carboxylic acid [3-(4-methyl-1H-imidazol-1-yl)-5-(trifluoromethylphenyl)]amide,
6-[[2-[[(diethylamino)carbonyl]amino]-pyridin-4-yl]oxy]-naphthalene-1-carboxylic acid [3-(4-methyl-1H-imidazol-1-yl)-5-(trifluoromethylphenyl)]amide,
6-[[2-[(2-Pyridinyl)amino]-4-pyridinyl]oxy]-naphthalene-1-carboxylic acid [3-(4-methyl-1H-imidazol-1-yl)-5-(trifluoromethylphenyl)]amide,
6-[2-(Cyclopropylcarbonyl)amino-pyridin-4-yloxy]-naphthalene-1-carboxylic acid [4-[(4-methyl-1-piperazinyl)methyl]-3-trifluoromethyl-phenyl]amide,
6-(2-Acetylamino-pyridin-4-yloxy)-naphthalene-1-carboxylic acid [4-[(4-methyl-1-piperazinyl)methyl]-3-trifluoromethyl-phenyl]amide,
6-[4-[[[5-[[2-[(Cyclopropylcarbonyl)amino]-4-pyridinyl]oxy]-1-naphthalenyl]carbonyl]amino]-2-(trifluoromethyl)phenyl]-1-piperazinecarboxylic acid, phenylmethyl ester,
6-[[2-(Cyclopropanecarbonyl-amino)-pyridin-4-yl]oxy]-naphthalene-1-carboxylic acid (3-piperazin-1-yl-5-trifluoromethyl-phenyl)-amide,
6-[[2-(Cyclopropanecarbonyl-amino)-pyridin-4-yl]oxy]-naphthalene-1-carboxylic acid [4-(9-methyl-3,9-diazabicyclo[3.3.1]non-3-ylmethyl)-3-trifluoromethyl-phenyl]-amide,
6-[[2-(Cyclopropylcarbonyl)amino-pyridin-4-yl]oxy]-naphthalene-1-carboxylic acid [3-(1-methyl-1H-imidazol-1-yl)-5-(trifluoromethylphenyl)]amide,
6-[[2-(Cyclopropylcarbonyl)amino-pyridin-4-yl]oxy]-naphthalene-1-carboxylic acid [3-(1,2-dimethyl-1H-imidazol-1-yl)-5-(trifluoromethylphenyl)]amide,
6-[[2-(Cyclopropylcarbonyl)amino-pyridin-4-yl]oxy]-naphthalene-1-carboxylic acid [3-[1-(phenylmethyl)-2-dimethyl-1H-imidazol-1-yl]-5-(trifluoromethylphenyl)]amide,
6-[[2-(Cyclopropylcarbonyl)amino-pyridin-4-yl]oxy]-naphthalene-1-carboxylic acid [3-(2-methyl-1H-imidazol-1-yl)-5-(trifluoromethylphenyl)]amide,
6-[[6-(Amino)-4-pyrimidinyl]oxy]-N-[4-[(4-methyl-1-piperazinyl)methyl]-3-(trifluoromethyl)phenyl]-1-naphthalenecarboxamide,
6-(6-Acetylamino-pyrimidin-4-yloxy)-naphthalene-1-carboxylic acid [3-(4-methyl-imidazol-1-yl)-5-trifluoromethyl-phenyl]-amide, 6-[6-(Cyclopropanecarbonyl-amino)-pyrimidin-4-yloxy]-naphthalene-1-carboxylic acid [3-(4-methyl-imidazol-1-yl)-5-trifluoromethyl-phenyl]-amide, 6-(6-Acetylamino-pyrimidin-4-yloxy)-isoquinoline-1-carboxylic acid [4-(4-methyl-piperazin-1-ylmethyl)-3-trifluoromethyl-phenyl]-amide, 6-(6-Amino-pyrimidin-4-yloxy)-naphthalene-1-carboxylic acid [4-(4-methyl-piperazin-1-ylmethyl)-3-trifluoromethyl-phenyl]-amide, 7-(6-Acetylamino-pyrimidin-4-yloxy)-isoquinoline-4-carboxylic acid [4-(4-methyl-piperazin-1-ylmethyl)-3-trifluoromethyl-phenyl]-amide, 6-(6-Amino-pyrimidin-4-yloxy)-naphthalene-1-carboxylic acid [3-(4-methyl-imidazol-1-yl)-5-trifluoromethyl-phenyl]-amide, 6-[(6-Amino-pyridin-4-yl)oxy]-naphthalene-1-carboxylic acid [3-(4-methyl-imidazol-1-yl)-5-trifluoromethyl-phenyl]-amide 6-[2-(Cyclopropanecarbonyl-amino)-pyridin-4-yloxy]-naphthalene-1-carboxylic acid [4-(9-methyl-3,9-diazabicyclo[3.3.1]non-3-ylmethyl)-3-trifluoromethyl-phenyl]-amide, 6-[2-(Cyclopropanecarbonyl-amino)-pyridin-4-yloxy]-naphthalene-1-carboxylic acid [3-(4-methyl-imidazol-1-yl)-5-trifluoromethyl-phenyl]-amide, 6-[2-(Cyclopropanecarbonyl-amino)-pyridin-4-yloxy]-naphthalene-1-carboxylic acid (3-piperazin-1-yl-5-trifluoromethyl-phenyl)-amide, 6-[[N-[2-(4-methyl-2-thiazolyl)amino]-pyridin-4-yl]oxy]-naphthalene-1-carboxylic acid [3-(4-methyl-1H-imidazol-1-yl)-5-(trifluoromethylphenyl)]amide, 6-[[2-[(1H-Imidazol-2-yl)carbonyl]amino-4-pyridinyl]oxy]-naphthalene-1-carboxylic acid [3-(4-methyl-1H-imidazol-1-yl)-5-(trifluoromethylphenyl)]amide, 6-[[2-[(2S)-2-Pyrrolidinecarbonyl]amino-pyridin-4-yl]oxy]-naphthalene-1-carboxylic acid [3-(4-methyl-1H-imidazol-1-yl)-5-(trifluoromethylphenyl)]amide, 6-[2-[(2S)-[1-[(1,1-Dimethylethoxy)carbonyl]-2-pyrrolidinecarbonyl]amino-pyridin-4-yloxy]-naphthalene-1-carboxylic acid [3-(4-methyl-1H-imidazol-1-yl)-5-(trifluoromethylphenyl)]amide, or a pharmaceutically acceptable salt thereof.

5. A pharmaceutical preparation comprising a compound of claim 1, or a pharmaceutically acceptable salt thereof, and at least one pharmaceutically acceptable carrier material.

6. A compound of the formula I, or a pharmaceutically acceptable salt thereof, according to claim 1, for the treatment of the animal or human body, wherein said treatment is of a diseases dependent on protein tyrosine kinases which is a leukemia.

7. A method of treatment of the human or animal body, wherein said treatment is of leukemia, comprising administering to a subject in need thereof a compound of the formula I, or a pharmaceutically acceptable salt thereof, according to claim 1.

8. A compound which is 6-[2-(Cyclopropanecarbonyl-amino)-pyridin-4-yloxy]-naphthalene-1-carboxylic acid [3-(4-methyl-imidazol-1-yl)-5-trifluoromethyl-phenyl]-amide, or a pharmaceutically acceptable salt thereof.

9. A compound selected from: 6-[[2-(Cyclopropylcarbonyl)amino-pyridin-4-yl]oxy]-isoquinoline-1-carboxylic acid [3-(4-methyl-1H-imidazol-1-yl)-5-(trifluoromethylphenyl)]amide; 6-[[2-(Cyclopropylcarbonyl)amino-pyridin-4-yl]oxy]-isoquinoline-1-carboxylic acid [3-(1-methyl-1H-imidazol-1-yl)-5-(trifluoromethylphenyl)]amide; and 7-(6-Acetylamino-pyrimidin-4-yloxy)-isoquinoline-4-carboxylic acid [4-(4-methyl-piperazin-1-ylmethyl)-3-trifluoromethyl-phenyl]-amide.

* * * * *